US010758695B2

(12) United States Patent
Krimsky et al.

(10) Patent No.: US 10,758,695 B2
(45) Date of Patent: Sep. 1, 2020

(54) ASSIST DEVICE FOR MEDICAL PROCEDURES

(71) Applicants: William Sanford Krimsky, Bel Air, MD (US); Curt Steven Kothera, Crofton, MD (US); Amit Navin Shah, Bethesda, MD (US); Gregory John Hiemenz, Silver Spring, MD (US)

(72) Inventors: William Sanford Krimsky, Bel Air, MD (US); Curt Steven Kothera, Crofton, MD (US); Amit Navin Shah, Bethesda, MD (US); Gregory John Hiemenz, Silver Spring, MD (US)

(73) Assignee: InnoVital LLC, Calverton, MD (US)

( * ) Notice: Subject to any disclaimer, the term of this patent is extended or adjusted under 35 U.S.C. 154(b) by 1070 days.

(21) Appl. No.: 15/024,832

(22) PCT Filed: Sep. 26, 2014

(86) PCT No.: PCT/US2014/057717
§ 371 (c)(1),
(2) Date: Mar. 24, 2016

(87) PCT Pub. No.: WO2015/050788
PCT Pub. Date: Apr. 9, 2015

(65) Prior Publication Data
US 2016/0220772 A1 Aug. 4, 2016

Related U.S. Application Data

(60) Provisional application No. 61/882,912, filed on Sep. 26, 2013.

(51) Int. Cl.
*A61M 16/04* (2006.01)
*A61M 27/00* (2006.01)
(Continued)

(52) U.S. Cl.
CPC ......... *A61M 16/0472* (2013.01); *A61B 90/10* (2016.02); *A61B 90/11* (2016.02);
(Continued)

(58) Field of Classification Search
CPC .......... A61M 16/0472; A61M 16/0493; A61M 16/0497; A61M 16/0683;
(Continued)

(56) References Cited

U.S. PATENT DOCUMENTS

| 3,791,386 A | * | 2/1974 | McDonald | ........ | A61M 16/0472 |
| | | | | | 128/207.29 |
| 3,991,765 A | * | 11/1976 | Cohen | ................ | A61M 16/0472 |
| | | | | | 128/207.29 |

(Continued)

OTHER PUBLICATIONS

Ivey, K.M., et al., 2012, "Thoracic injuries in US combat casualties: a 10-year review of Operation Enduring Freedom and Iraqi Freedom", Journal of Trauma Acute Care Surgery, 73(6 Suppl 5): S514-S519.

(Continued)

*Primary Examiner* — Colin W Stuart
*Assistant Examiner* — Douglas Y Sul
(74) *Attorney, Agent, or Firm* — Royal W. Craig; Gordon Feinblatt LLC

(57) ABSTRACT

A device to assist performing medical procedures that references anatomical landmarks through adjustable components to identify and stabilize a procedure site and provide guidance in performing the procedure. In one embodiment, an airway creation assist device (ACAD) can be dimensionally adjusted for different patient sizes and properly aligned using anatomical landmarks. The ACAD provides an adjustable template that enables accurate identification of the airway creation site, including but not limited to the cricothyroid membrane. The ACAD uses an insertion guide to guide the obturator and airway tube safely and consistently (Continued)

into the trachea, with a mechanical stop to prevent damaging the posterior trachea wall. The ACAD improves efficacy of the procedure, and makes perforating an incorrect airway creation procedure difficult. In another embodiment, a chest decompression assist device (DAD) Is disclosed for decompression treatment of air and/or fluid in the chest.

14 Claims, 19 Drawing Sheets

(51) Int. Cl.
  *A61B 90/10* (2016.01)
  *A61B 90/11* (2016.01)
(52) U.S. Cl.
  CPC ........ *A61M 16/0488* (2013.01); *A61M 27/00* (2013.01); *A61M 2205/583* (2013.01); *A61M 2205/6009* (2013.01); *A61M 2209/088* (2013.01); *A61M 2210/101* (2013.01); *A61M 2210/1032* (2013.01)
(58) Field of Classification Search
  CPC .... A61M 2209/088; A61M 2210/0618; A61M 5/427; A61B 2017/3407; A61B 2017/3405; A61B 90/10; A61B 90/11; A61B 90/14
  USPC .......................... 600/424, 587, 114; 606/130
  See application file for complete search history.

(56) References Cited

U.S. PATENT DOCUMENTS

| | | | | |
|---|---|---|---|---|
| 5,201,742 | A * | 4/1993 | Hasson | A61B 17/3403 606/1 |
| 5,339,809 | A | 8/1994 | Beck, Jr. et al. | |
| 7,169,129 | B2 * | 1/2007 | Gooden | A61M 16/0472 128/207.29 |
| 7,211,056 | B2 | 5/2007 | Petelenz et al. | |
| 7,267,124 | B1 | 9/2007 | Robertson et al. | |
| 7,347,840 | B2 | 3/2008 | Findlay et al. | |
| 7,373,939 | B1 | 5/2008 | DuBois et al. | |
| 8,151,791 | B2 | 4/2012 | Arlow et al. | |
| 8,535,251 | B1 | 9/2013 | Rao | |
| 2008/0251083 | A1 * | 10/2008 | Fetcenko | A61M 16/0472 128/207.29 |
| 2009/0229602 | A1 * | 9/2009 | Single, Jr. | A61B 17/32093 128/200.26 |
| 2009/0234255 | A1 | 9/2009 | Votel | |
| 2011/0040304 | A1 * | 2/2011 | Li | A61B 90/11 606/130 |

OTHER PUBLICATIONS

Aylwin, C.J., "Pre-Hospital and In-Hospital Thoracostomy: Indications and Complications", Annals of the Royal College of Surgeons of England, 90(1): 54-57 (2008).

Netto FA et al., "Are needle decompressions for tension pneumothraces being performed appropriately for appropriate indications?", American Journal of Emergency Medicine 26:597-602 (2008).

Eastridge, Brian et al., Death on the Battlefield (2001-2011): Implications for the Future of Combat Casualty Care, Jnl of Trauma and Acute Care Surgery, vm 73, Issue 6, pp. S431-S437 (Dec. 2012).

MacIntyre, A., Markarian, M. K., Carrison, D., Coates, J., Kuhls, D., and Fildes J. J., "Three-Step Emergency Cricothyroidotomy", Military Medicine, 172(12): 1228-1230 (2007).

Hsiao, S. and Pacheco-Fowler, V., "Cricothyroidotomy," New England Journal of Medicine, 358(22) 25 (2008).

Clancy, M. J., "A Study of the Performance of Cricothyroidotomy on Cadavers Using the Minitrach II", Archives of Emergency Medicine, 6: 143-145 (1989).

Benkhadra, M., Lenfant, F., Menetz, W. Anderhuber, F., Feigl, G., and Fasel, J., "A Comparison of Two Emergency Cricothyroidotomy Kits in Human Cadavers", International Anesthesia Research Society, 106(1): 182-185 (2008).

Mabry, R. L. and Frankfurt, A., "An Analysis of Battlefield Cricothyrotomy in Iraq and Afghanistan", Journal of Special Operations Medicine, 12(1): 17-23 (2012).

Ivey, K. M., et al, "Thoracic injuries in US combat casualties: a 10-year review of Operation Enduring Freedom and Iraqi Freedom," Journal of Trauma Acute Care Surgery, 73(6 Suppl 5): S514-S519, 2012.

Aylwin, C. J., "Pre-Hospital and In-Hospital Thoracostomy: Indications and Complications," Ann R Coll Surg Engl, 90(1): 54-57; 2008.

Fernando Antonio Campelo Spencer Netto et al. , "Are needle decompressions for tension pneumothraces being performed appropriately for appropriate indications?" The American Journal of Emergency Medicine, 26: 597-602 (2008).

Bennett, B. L., Cailteux-Zevallos, B., and Kotora. J., "Cricothyroidotomy Bottom-Up Training Review: Battlefield Lessons Learned," Military Medicine, 176(11): 1311-1319 (2011).

Murphy, C., Rooney, S. J., Maharaj, C. H., Laffey, J. G., and Harte, B. H., "Comparison of Three Cuffed Emergency Percutaneous Cricothyroidotomy Devices to Conventional Surgical Cricothyroidotomy in a Porcine Model," British Journal of Anaesthesia, 106(1): 57-64 (2011).

Walsh, R, Hiener, J., Kang, C., Hile, D., and Deering, S., "Emergency Physician Evaluation of a Novel Surgical Cricothyroidotomy Tool in Simulated Combat and Clinical Environments", Military Medicine, 178(1): 29-33 (2013).

* cited by examiner

ASSIST DEVICE FOR MEDICAL PROCEDURES

BACKGROUND OF THE INVENTION

1. Field of the Invention

The present invention generally relates to medical devices for performing medical procedures, such as a cricothyrotomy, thoracostomy, or chest decompression and/or drainage and more particularly, to an airway creation assist device (AACAD) for proper identification of the airway tube insertion site, proper incision into or puncture of the trachea, proper placement and securement of an airway tube, and securing the tube in place. A chest decompression assist device is also disclosed for the drainage of air and/or fluid from the chest.

2. Description of Prior Art

Studies suggest that many wartime casualties could be avoided if interim tools and procedures could be implemented to allow non-experts to perform certain procedures before the injured patient can be transported to a surgeon. For example, obstruction of the airway is still one of the most common preventable causes of death on the battlefield. Eastridge, Brian et al., "*Death on the Battlefield* (2001-2011): *Implications For The Future Of Combat Casualty Care*, Jnl of Trauma and Acute Care Surgery, vm 73, Issue 6, pp S431-S437 (December, 2012). Cricothyrotomy (also called thyrocricotomy, cricothyroidotomy, inferior laryngotomy, intercricothyrotomy, coniotomy or emergency airway puncture) is a medical procedure wherein an incision is made through the skin and cricothyroid membrane to establish a patent airway during certain life-threatening, situations when trauma or obstructions prevent more common, less traumatic air ix management techniques, e.g., orotracheal or nasotracheal intubation. There are two commonly accepted types of cricothyrotomy procedures: (1) surgical cricothyrotomy and (2) percutaneous cricothyrotomy. In the surgical type, a scalpel is used to make an incision in the skin and through the cricothyroid membrane, into the trachea, which is then opened to insert a cricothyrotomy tube, in the percutaneous type, a needle that extends through a catheter is inserted through the cricothyroid membrane and into the trachea. After reaching the trachea, the catheter is advanced along the inserted needle, into the trachea, and then the needle is removed. Examples of the percutaneous approach are the modified Seldinger technique and direct airway placement. The surgical cricothyrotomy has been the preferred technique in combat. MacIntyre, A., Markarian, M. K., Carrison, D., Coates, J., Kuhls, D., and Fildes J. J., "*Three-Step Emergency Cricothyroidotomy*", Military Medicine, 172(12): 1228-1230 (2007). Regardless of the type of procedure employed, locating the cricothyroid membrane is critical in performing the procedure effectively. For this reason, relative to the subject invention, "percutaneous" is herein defined as any through-the-skin approach: catheter over needle, surgical, open dissection, etc. Anatomical landmarks are used to manually locate the cricothyroid membrane, such as the thyroid cartilage and laryngeal prominence (Adam's apple). Complications can arise in performing the procedure, however, including esophageal perforation, subcutaneous emphysema, and hemorrhage. Hsiao, S. and Pacheco-Fowler, V., "*Cricothyroidotomy*," New England Journal of Medicine, 358(22) 25 (2008). The more common mistakes or failures in performing cricothyrotomies are related to improper placement and improper insertion depth. Difficulties have been reported in maintaining correct alignment between the incision in the skin tissue and the cricothyroid membrane using the standard surgical procedure, for example, which can lead to cutting into or introducing a catheter into tissue adjacent to the trachea, rather than the trachea itself. Clancy, M. J., "*A Study Of The Performance Of Cricothyroidotomy On Cadavers Using The Minitrach II*", Archives of Emergency Medicine, 6: 143-145 (1989). Moreover, lesions and even perforations of the posterior tracheal wall are a common complication related to incorrect insertion depth of the needle and/or catheter, the prevalence of which can vary depending on the type of tools used in performing the cricothyrotomy. Benkhadra, M., Lenfant, F., Menetz, W. Anderhuber, F., Feigl, G., and Fasel, J., "*A Comparison of Two Emergency Cricothyroidotomy Kits in Human Cadavers*", International Anesthesia Research Society, 106(1): 182-185 (2008).

It has been reported from recent conflicts in Iraq and Afghanistan that only 68% of pre-hospital cricothyrotomies were successful, and that this nearly ⅓ chance of failure from military medics was more than twice the failure rate (15%) of physicians or physician assistants. Mabry, R. L. and Frankfurt, A., "*An Analysis of Battlefield Cricothyrotomy in Iraq and Afghanistan*", Journal of Special Operations Medicine, 12(1): 17-23 (2012).

Even more prevalent are thoracic injuries, which occurred in nearly 10% of wounded personnel in recent military engagements. Ivey, K. M., et al., 2012 "*Thoracic injuries in US combat casualties: a* 10-year review of Operation Enduring Freedom and Iraqi Freedom," Journal of Trauma Acute Care Surgery, 73(6 Suppl 5): S514-S519. Tension pneumothorax, consequence of thoracic trauma, is among the top three most common causes of preventable combat death. Eastridge, Brian et al., "*Death on the Battlefield* (2001-2011): *Implications For The Future Of Combat Casualty Care*, Jnl of Trauma and Acute Care Surgery, vm 73, Issue 6, pp S431-S437 (December 2012). The medical procedure of tube thoracostomy, also known as chest tube decompression or intercostal drain, is the most definitive initial treatment to manage thoracic injury. This procedure is likewise commonly performed incorrectly, with tube malposition occurring over 30% of the time, and the most frequent major complication associated with tube thoracostomy is non-relieved tension pneumothorax. Aylwin, C. J., 2008. "*Pre-Hospital and In-Hospital Thoracostomy: Indications and Complications,*" Ann R Coll Surg Engl, 90(1): 54-57. In the related needle decompression, high failure rates have been reported with over 40% resulting from incorrect needle location. Netto, F. A. C. S., et al., "*Are needle decompressions for tension pneumothoraces being performed appropriately for appropriate indications?*" The American Journal of Emergency Medicine, 26: 597-602 (2008). One approach to performing chest decompression has the user insert the medical instrument (e.g., needle) in an area under the axilla (armpit) delineated by a horizontal line at the nipples and the latissimus dorsi and pectoralis major. Here as well erroneous placement of the needle increases the risk of damage to internal blood vessels and mediastinal structures.

Contributors to procedural failure on the battlefield include limited training and experience of combat medics relative to physicians, and the battlefield environment itself, it has been shown, for example, that stressful conditions can adversely affect clinical skill. Moorthy, K., Munz, Y., Dosis, A., Bannm, S., Darzi, A., "*The Effect Of Stress-Inducing Conditions On The Performance Of A Laparoscopic Task*," Surgical Endoscopy, 17(9): 1481-1484 (2003). There is likely no condition more stressful than a battlefield. Since the procedure may need to be performed by combat medics or fellow soldiers, as simplified and more reliable procedure is imperative. The 15% failure rate observed with physicians and physician assistants performing this emergency lifesaving procedure indicates a need for improving the procedure for more skilled providers as well. Realizing this need, as recent review of tactical combat casualty care has identified five areas in need of improvement related to the procedure: (1) limited anatomy knowledge and inadequate transfer to practical skill; (2) lack of hands-on anatomy familiarization; (3) nonstandardized procedure; (4) inferior industry standard for training mannequins; and (5) lack of refresher training. Bennett, B. L., Cailteux-Zevallos, B., and Kotora. J., "*Cricothyroidotomy Bottom-Up Training Review: Battlefield Lessons Learned*," Military Medicine, 176(11): 1311-1319 (2011).

Several kits have been developed in an attempt to simplify the procedure or reduce the number of tools needed, but none have demonstrated statistically significant improvement above the standard issue cricothyrotomy kits (surgical method). For example, Chinook Medical sells an emergency cricothyrotomy kit that contains a scalpel, cuffed endotracheal tube, syringe, curved hemostat, and tracheal hook. The Rüsch QuickTrach® cricothyrotomy kit has fewer individual parts, presumably simplifying the procedure, but this comes at the expense of a more complicated and costly whole. The CRIC™ device from Pyng Medical is a multi-tool designed for military use that incorporates a clipped-in sterilizing wipe, tie-down strap, light, tissue spreader, and retractable scalpel into a single small tool.

A number of these kits were recently compared in a porcine model study using, participants that were trained in surgical cricothyrotomy, but untrained with the three different kits evaluated. Murphy, C., Rooney, S. J., Maharaj, C. H., Laffey, J. G., and Harte, B. H., "*Comparison Of Three Cuffed Emergency Percutaneous Cricothyroidotomy Devices To Conventional Surgical Cricothyroidotomy In A Porcine Model*," British Journal of Anaesthesia, 106(1): 57-64 (2011). While one of the kits was subjectively rated as being slightly easier to use than the standard surgical tools, it took over 50% longer to complete the procedure with the "easier" kit than with the standard surgical kit (94 sec vs. 59 sec) in an operating room environment. This duration is similar to a second reported study (54 s) in an operating room environment for the surgical procedure, thereby establishing a baseline between the two studies. The second study also compared results of simulated combat environments. Walsh, R, Hiener, J., Kang, C., Hile, D., and Deering, S., "*Emergency Physician Evaluation of a Novel Surgical Cricothyroidotomy Tool in Simulated Combat and Clinical Environments*", Military Medicine, 178(1): 29-33 (2013). These findings showed that the average time thin reaching a patient to achieving successful intubation with the surgical method was approximately 45 sec, which is 17% faster, but a greater complication rate was reported.

In addition to successfully performing a cricothyrotomy, these studies highlight two other related aspects. The first is that the number of tools in the kit is not directly proportional to the time required for task completion or complication rate, and the second is that stressful environments (e.g., combat) may reduce efficacy. It is therefore paramount that a truly effective cricothyrotomy device or kit be easy to use and intuitive, considerations which have proven to be unattainable for the standard surgical kit. Mabry. R. L. and Frankfurt, A., "*An Analysis of Battlefield Cricothyrotomy in Iraq and Afghanistan*", Journal of Special Operations Medicine, 12(1): 17-23 (2012). These studies also call attention to another important metric, which is the amount of time required to establish an airway (more than 300 sec was considered failure).

Based upon this brief review of emergency cricothyrotomies, it can be concluded that the primary factors affecting the efficacy of the procedure, are: (1) proper identification of the insertion site, (2) proper incision into or puncture of the trachea, (3) proper insertion of the cricothyrotomy tube (including both placement and securement), and (4) time to cricothyrotomy tube placement.

The previous discussion has elucidated the fact that none of the existing cricothyrotomy kits perform noticeably better than the standard surgical kit, if not worse, and given the high reported failure rate in combat situations when using the standard, multi-part surgical kit, a new solution is motivated.

While much of this discussion has focused on cricothyrotomy, this is because a number of tools have been developed in attempts to improve this particular procedure. The far more common procedure chest decompression and drainage has regretfully experienced far less effort for improvement and there are no existing tools that aid the user in identifying the proper insertion site.

Other prior art has attempted to address some of these noted issues for cricothyrotomies or related procedures. For example, U.S. Pat. No. 3,791,386 (McDonald) shows a tracheotomy assist device for those lacking medical training that includes an indexing frame with a chinrest that is secured to the patient's neck and a rotation knob that pokes three holes into the trachea. U.S. Pat. No. 3,991,765 (Cohen) shows a cricothyrotomy apparatus that performs the procedure automatically with a spring-loaded blade and spring-loaded tube contained in a housing. U.S. Pat. No. 7,267,124 (Robertson et al.) shows a kit to facilitate tracheostomies that includes a template guide to place on a patient to indicate the incision location, a cutting instrument, and a breathing tube. U.S. Pat. No. 7,347,840 (Findlay et al.) shows an apparatus for locating a site of intraosseous infusion that includes an adhesive template patch with a target zone located a predetermined distance away from an anatomical feature. U.S. Pat. No. 8,151,791 (Arlow et al.) shows a tracheotomy device with a curved dilator with an inner passageway that acts as an anchor, U.S. Pat. No. 7,373,939 (DuBois et al.) shows an integrated tracheotomy tool using a pistol-grip impact-driven trocar delivery mechanism that can be actuated impulsively.

Aside from the fact that cricothyrotomies are fundamentally different procedures than tracheostomies and tracheotomies, particularly in emergency situations such as on the battlefield, none of this prior art adequately addresses all of the underlying problem areas. As noted above, the same is true for other medical procedures, such as tube thoracostomies and needle decompression. What is needed is an assist device for guiding medical procedures, including cricothyrotomies, needle decompression, tube thoracostomies, and other percutaneous procedures with universal applicability that significantly improves the success rate and effectiveness of performing the procedures.

SUMMARY OF THE INVENTION

In accordance with the foregoing objects, it is an object of the present invention to provide an assist device for medical procedures that uses physical reference points of the anatomy for alignment, stabilization, and guidance of surgical took such as, but not limited to needle, scalpel, retractor, forceps, and/or catheter.

It is another object to provide a airway creation assist device (ACAD) that is easy-to-use, designed with failsafe features to avoid both common and devastating errors, that is effective and broadly applicable. The airway creation procedure may be a cricothyrotomy or tracheostomy.

It is another object to provide an adjustable ACAD that uses physical reference points of the anatomy (i.e., anatomical landmarks) for alignment, stability, and tube placement.

It is another object to provide an ACAD that may be used by users of different skill levels.

It is still another object to provide a decompression assist device (DAD) for drainage of air and fluid from the chest with the foregoing advantages, likewise using physical reference points of the anatomy for alignment, stabilization, and guidance of surgical tools.

In accordance with the foregoing and other objects, the present invention is an all-in-one, lightweight, packable airway creation assist device that can be dimensionally adjusted for different patient sizes and properly aligned and stabilized using anatomical landmarks. The ACAD provides an adjustable template that enables accurate identification of the proper procedure site, such as the cricothyroid membrane. The ACAD features an insertion guide to guide the obturator and airway tube safely and consistently into the trachea, with a mechanical stop to prevent damaging the posterior trachea wall. Once in place, the ACAD is easily and safely removable without dislodging the tube, after which the tube can be further secured according to standard practice. The ACAD may be color-coded and numbered/labeled for intuitive ease of use regardless of skill level or training experience.

The ACAD of the present invention improves efficacy of the procedure, and makes performing an airway creation procedure incorrectly difficult, such as a cricothyrotomy. Similarly, the DAD of the present invention provides procedural guidance to enable successful, complication-free chest decompression and drainage.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

The present invention is an assist device for performing medical procedures.

In one embodiment, an adjustable airway creation assist device (ACAD) is disclosed which uses physical reference points of the anatomy for alignment, stabilization, and intubation guidance, whereas the medical procedure to create the airway may be a cricothyrotomy or tracheostomy. The ACAD is easy-to-use by both skilled and unskilled personnel, highly effective, and has broad applicability. In another embodiment, a chest decompression assist device is disclosed for drainage of air or liquid from the chest which uses physical reference points of the anatomy for alignment, stabilization, and decompression needle guidance.

Figure 1:
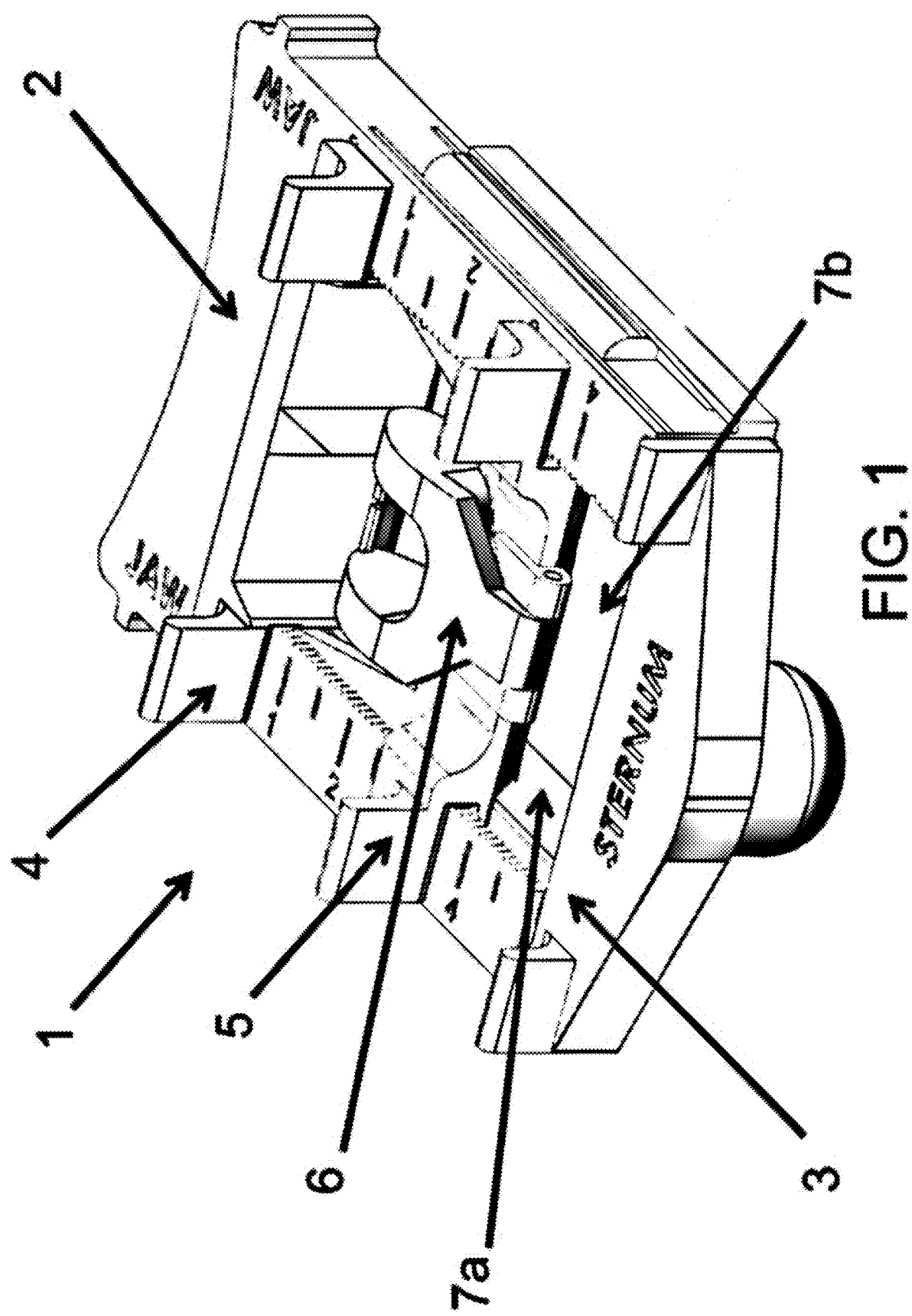
FIG. 1 is a top perspective illustration of the preferred embodiment of the universal airway creation assist device 1 in a compact packaged configuration.
Figure 2:
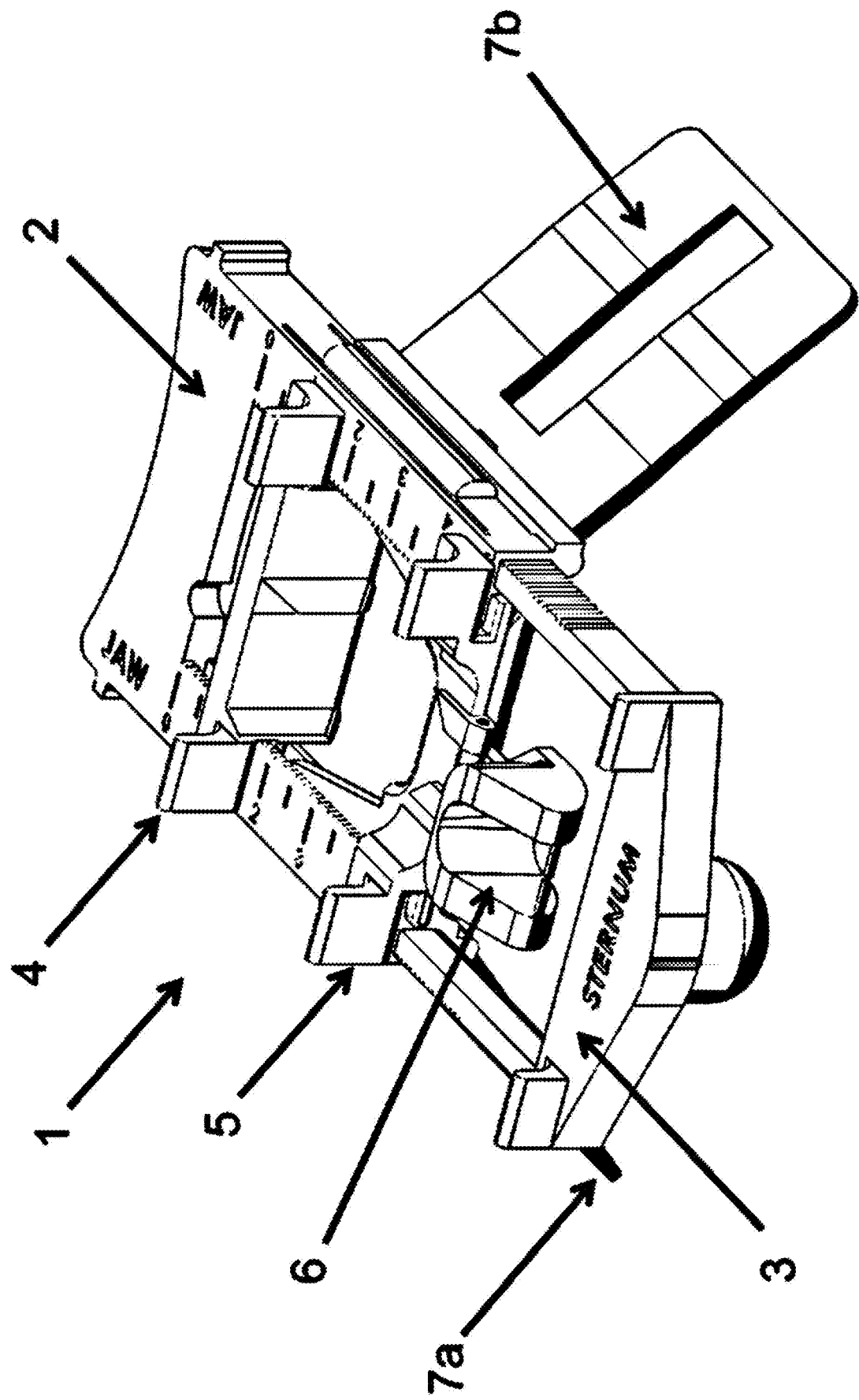
FIG. 2 is a top perspective illustration of the preferred embodiment of the airway creation assist device 1 in a deployed operational configuration.
Figure 3:
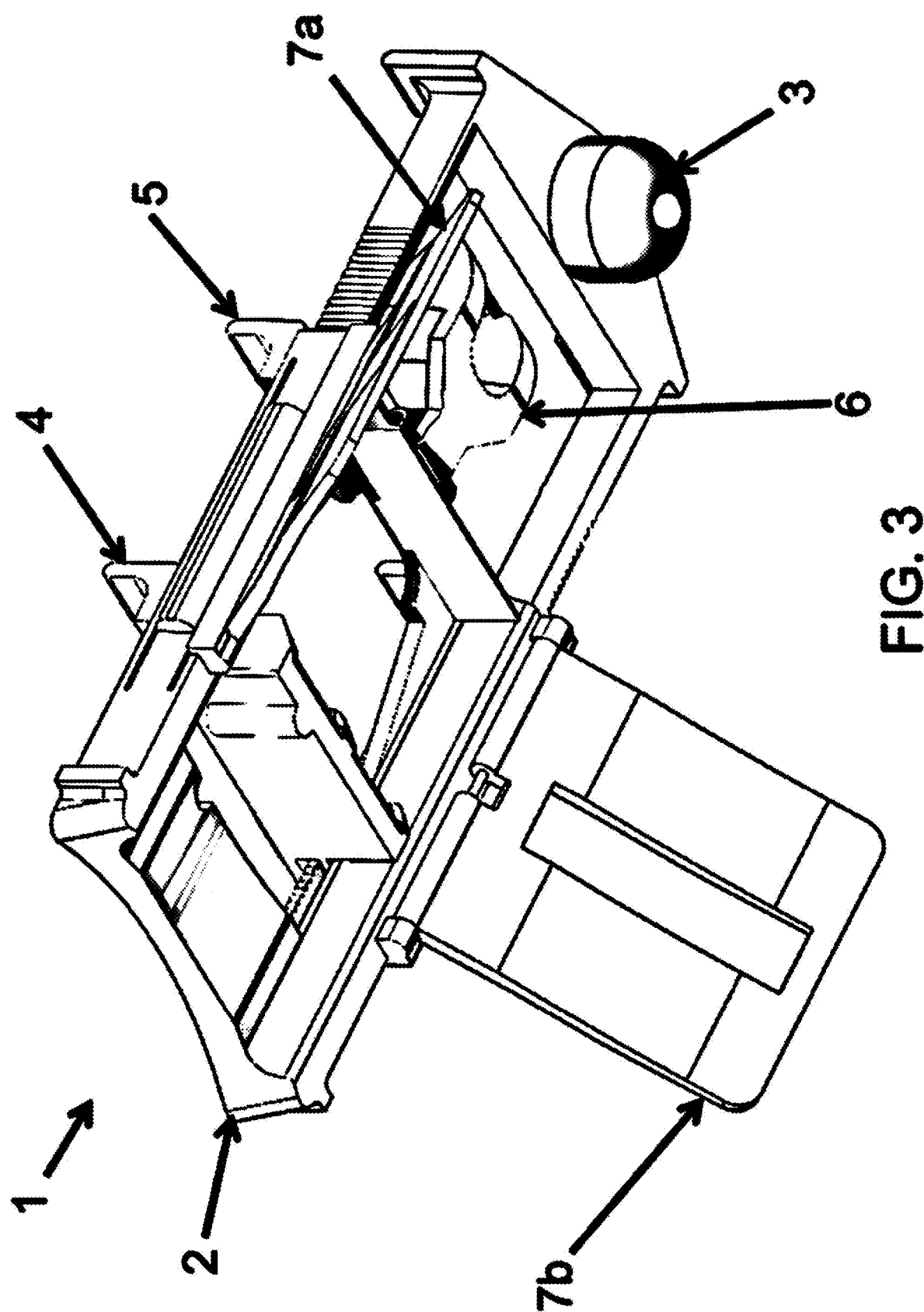
FIG. 3 is a bottom perspective illustration of the preferred embodiment of the airway creation it device 1 in a deployed operational configuration.
Figure 4:
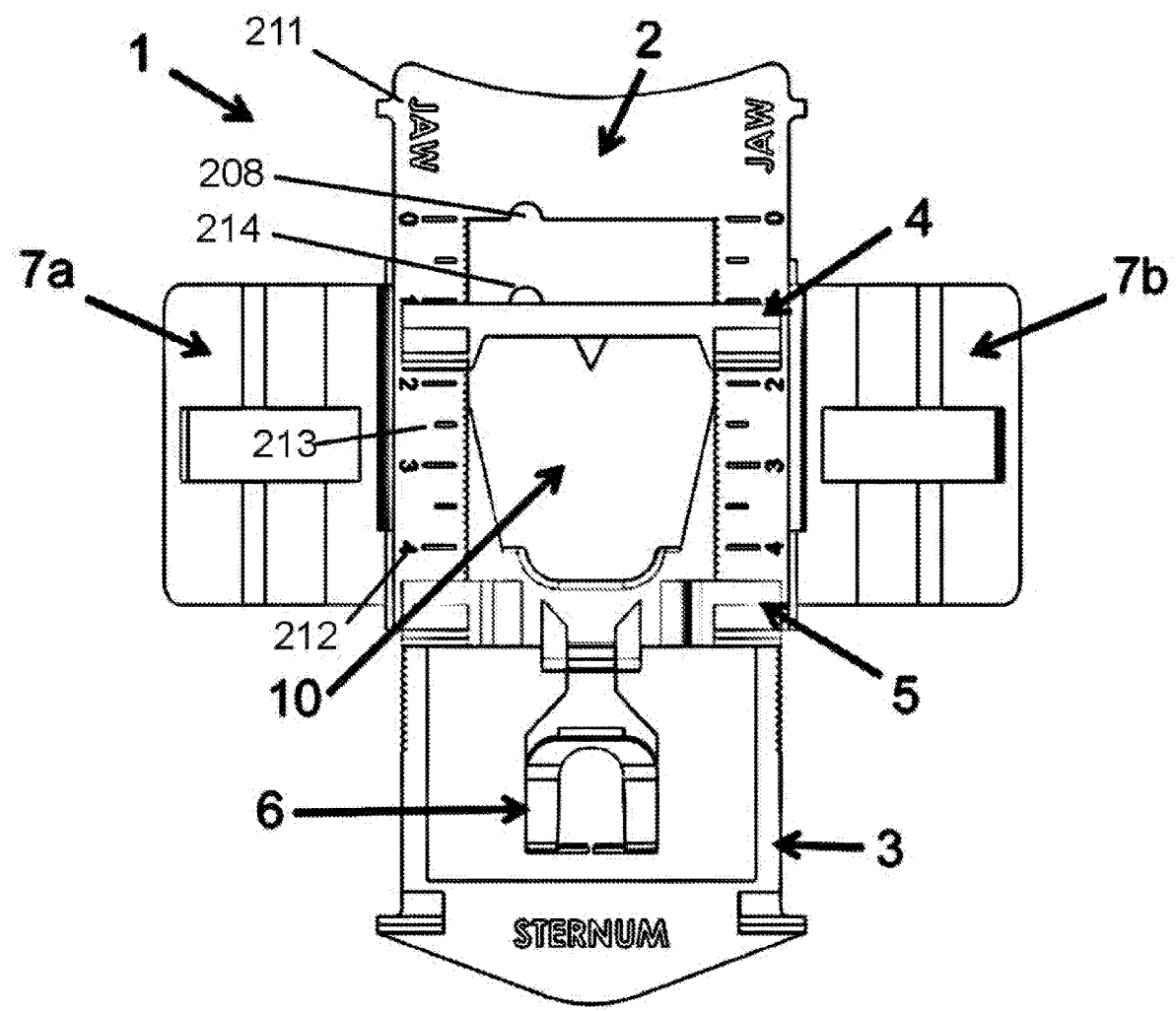
FIG. 4 is a top view illustration of the preferred embodiment of the airway creation assist device 1 in a deployed operational configuration.

As seen in FIGS. 1-4, a preferred embodiment of the assist device comprises a ACAD 1 including a laryngeal base 2, a sternal stabilizer 3, a thyroid locator 4, a cricoid locator 5, an insertion guide 6, and two lateral stabilizers 7 (a & b). The laryngeal base 2 forms the infrastructure of the ACAD device 1 and all noted components integrate with it directly or indirectly. The ACAD device 1 articulates from a compact configuration to as stowed configuration. The compact or stowed configuration of the device 1 is displayed in FIG. 1 and an operational configuration is displayed in FIG. 2. FIG. 3 is a bottom perspective illustration and FIG. 4 is a top view both in the deployed operational configuration of FIG. 2.

Figure 5:
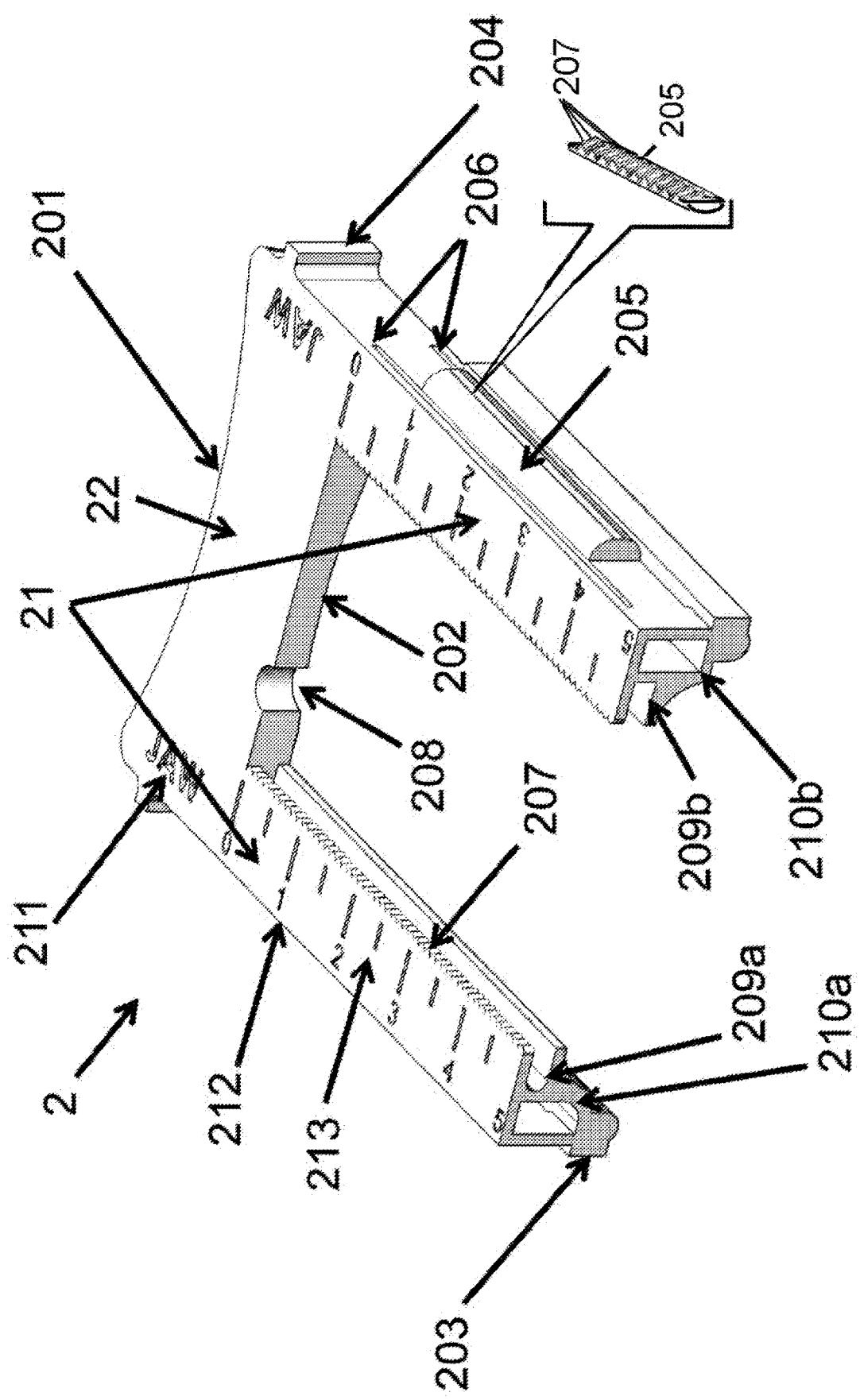
FIG. 5 is a top perspective illustration of the laryngeal base 2 of the airway creation assist device 1 of FIGS. 1-4.

FIG. 5 is a standalone view of the laryngeal base 2 of FIGS. 1-4, and illustrates its two longitudinal spans 21 bridged by a lateral span 22 at the superior end. The posterior surface of the lateral span 22 at the superior end is defined by a concave, approximately semi-cylindrical yoke 202 dimensioned to conform to the anatomical curvature of the neck. Curvature is also provided on the superior surface 201 to conform to the patient below and between the mandible. The two longitudinal spans 21 are bounded on at least three sides and thereby define internal channels 210 (a & b) which serve as receptacles for the arms of sternal stabilizer 3 as described below. The two longitudinal spans 21 also have inner tracks 209a, 209b extending horizontally along the interior of the laryngeal base 2 for slidably seating, the thyroid locator 4 and cricoid locator 5 (FIGS. 1-2). Both longitudinal spans 21 are demarcated with topside gridlines 213 and/or measuring indicia 212 to visually gauge sliding displacement of the thyroid locator 4 and cricoid locator 5 within tracks 209a, 209b, in addition, the lateral span 22 at the superior end of base 2 has an annotation 211 marked "JAW" to inform the user as to what anatomical feature the lateral span 22 is to be aligned with and providing information on proper device orientation with respect to the patient.

Laryngeal base 2 may also feature other annotations to provide the user with more information, such as hash marks 213 that provide reference information for how far the thyroid locator 4 and cricoid locator 5 have been moved from their stowed configuration (FIG. 1) to their operationally deployed configuration (FIG. 2) and their relative placement from one another. Units are not shown attached to the hash mark labels 212 in the figures, but the labels preferably have centimeter spacing attached to remain consistant with similar labeling on other medical devices.

Laryngeal base 2 also preferably has asymmetrical design features that coincide with similarly asymmetrical design features liar direct mating with the other components including sternal stabilizer 3, thyroid locator 4, and cricoid locator 5. For example, internal channel 209a and 209b may be sized and/or shaped differently to prevent longitudinal spans 309 of sternal stabilizer 3 from being assembled incorrectly. For example, in FIG. 5 the rounded corner of channel 209a of laryngeal base 2 integrates with rounded corner 310a of longitudinal span 309a of sternal stabilizer 3 in only one way, which ensures that the components are properly oriented. Similarly liar the other side rectangular corners 310b of longitudinal span 309b of sternal stabilizer 3 only fit into rectangular channel 2091 of laryngeal base. While one rounded corner was used to illustrate the asymmetry here, it is obvious that any other asymmetry would serve the same purpose, such as different geometric shapes or different sizes of integrating members.

Other asymmetric design features may also be included into the components. For example, an off-center notch 208 may be added to the lateral span 22 of laryngeal base 2, such that thyroid locator 4 only integrates correctly in one orientation via a male-counterpart feature 408 that his into off-center notch 208. While this alone may suffice for fool-proof assembly or re-assembly, redundant measures are preferred since cricothyrotomies are commonly performed under situational duress. As such, inner channels 209a and 209b of laryngeal base 2 are shown as asymmetric, with rounded corners and rectangular corners, respectively, which prevent improper orientation of thyroid locator 4 via asymmetrical tabs 409a and 409b (see FIG. 7) and cricoid locator 5 via asymmetrical tabs 509a and 509b (FIG. 8).

To facilitate relative component adjustments, laryngeal base 2 may also feature lateral extensions 204 to provide resistance force in the opposite direction to component movement, such as when extending sternal stabilizer 3 in the caudad direction. While lateral extensions is pictured in the preferred embodiment (see FIG. 5), this is not meant to limit the invention where someone skilled in the art could obviously replace the extensions with another feature, such as depressions, which serve the same purpose.

Regarding relative components adjustment and the intended stability to be added to the procedure by ACAD device 1, the lateral outer faces of internal channels 210 may be formed into flexible detent members 205 by cutting channels 206 from the outer lateral surface to the inner lateral surface of the channels such thin flexible detest member 205 moves under lateral or medial applied pressure. The inner surface of flexible detent member 205 may also contain surface features, such as teeth 207 as shown in the inset of FIG. 5, that lockingly engage cooperating features on the adjustable components, for example, rounded teeth 305 on the outer lateral surface of the longitudinal spans 309 of sternal stabilizer 3 as seen and described in FIG. 6 below.

The sternal stabilizer 3 is extendable/retractable from/to laryngeal base 2 and is articulated for longitudinal adjustment perpendicular to the lateral span 22 at the superior end of base 2.

Figure 6:
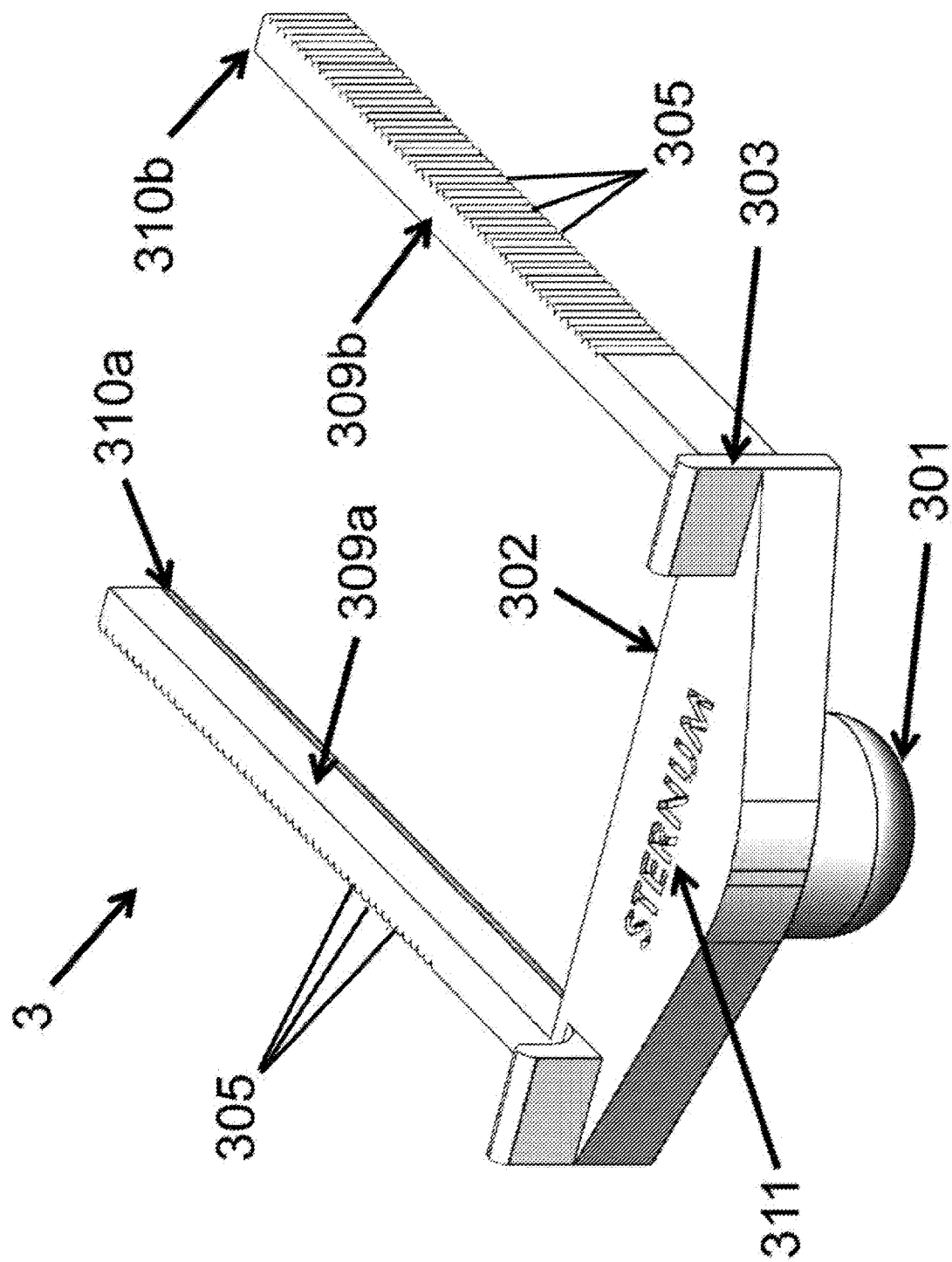
FIG. 6 is a top perspective illustration of the sternal stabilizer 3 of the airway creation assist device 1 of FIGS. 1-4.

FIG. 6 is a standalone view of the sternal stabilizer 3 of FIGS. 1-4, and illustrates its two longitudinal spans 309a, 309b bridged by a lateral span 302 at the inferior end. As indicated above the two longitudinal spans 309a, 309b may be defined by outer surface features such as rounded teeth 305 to releasably engage cooperating features on the inner surface of flexible detent member 205 (FIG. 5 inset). The lateral span 302 supports a sternal tab 301 that is shaped as a rounded-end downwardly-protruding post for positioning against the manubrium of the sternum, commonly referred to as the sternal notch. The lateral span 302 may also contain an informative annotation 311, such as being marked "STERNUM" to inform the user as to what anatomical feature the lateral span 302 is to be aligned with, and also providing information as to correct orientation of the device relative to the patient. A pair of finger tabs 303 project upwardly and laterally on opposing sides of the lateral span 302 to facilitate insertion/extraction from base 2, in much the same way a extensions 204 on laryngeal base 2.

The sternal tab 301 protrudes dorsally and downwardly from the sternal stabilizer 3 to provide caudal stability, index the location of the sternal manubrium, and maintain mid-line alignment of the neck and trachea. By inserting or extracting the lateral span 302 from laryngeal base 2 as necessary to position sternal tab 301 over the sternal manubrium, the sternal stabilizer 3 effectively provides an adjustable spacer against the sternal manubrium so that the ACAD device 1 can be universally applied to patients with various neck lengths, using the sternal manubrium as the physical reference point. Also, when seated anterior to the trachea and thyroid cartilage, the sternal stabilizer 3/laryngeal base 2 provide lateral and cephalo-cauadad stability to the procedure, and uses the manubrium of the sternum for caudal stability, in tandem with the sternocleidomastoid muscles for lateral stability at the distal end.

Referring back to FIGS. 1-4, two lateral stabilizers 7 are pivotally attached on opposing sides of the laryngeal base 2 for additional lateral adjustment and stability.

Figure 10:
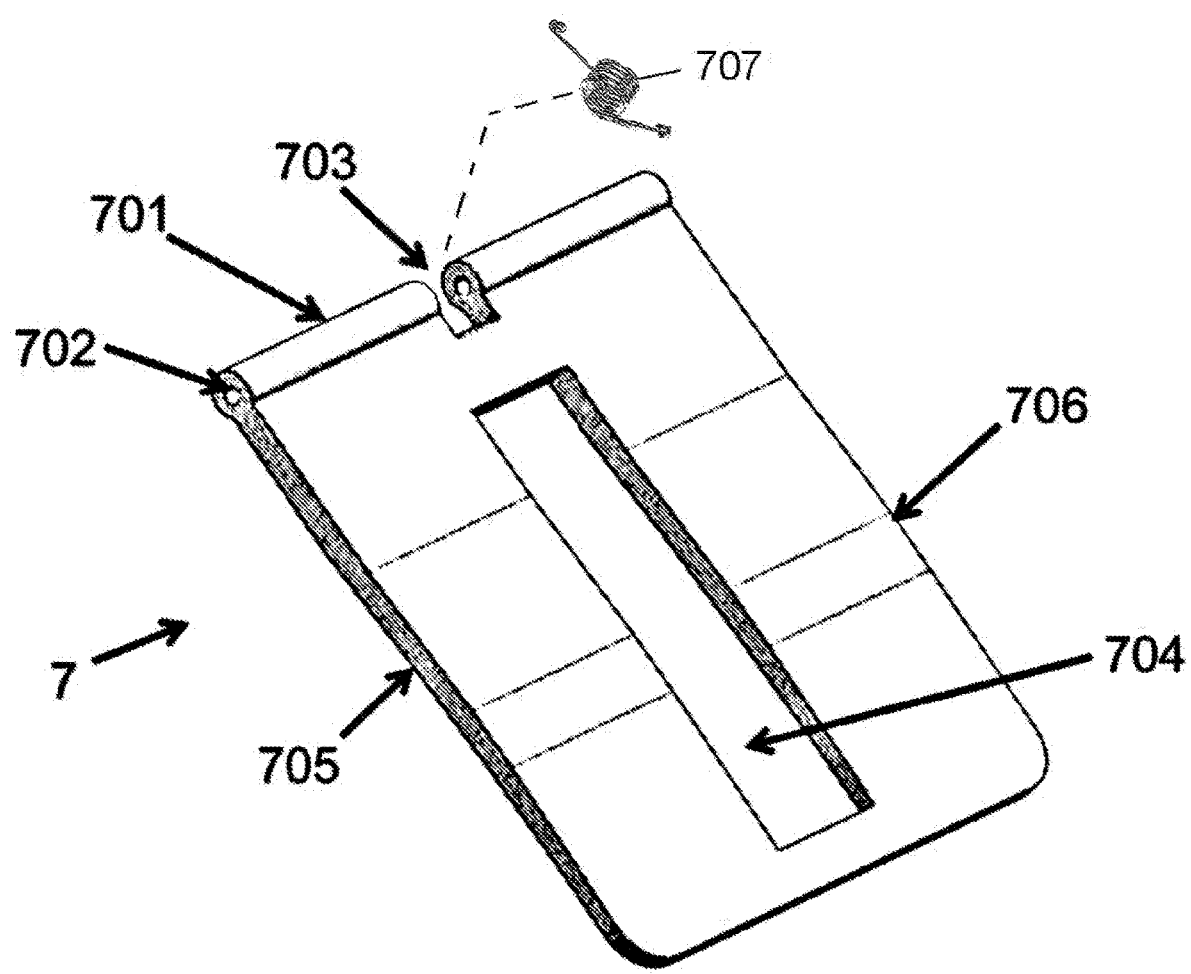
FIG. 10 is a top perspective illustration of the lateral stabilizer 7 of the airway creation assist device 1 of FIGS. 1-4.

FIG. 10 is a standalone view of an exemplary lateral stabilizer 7 which generally comprises a fold-down substantially-flat rectangular flap pivotally-hinged to the side of the of the laryngeal base 2. The lateral stabilizer 7 may be defined by posterior (patient side) and anterior (user contact side) surfaces 705 and 706, respectively, both of which may feature ergonomic contour and surface finishes to facilitate stabilizing the procedure, such as non-slip surfaces. The two lateral stabilizers 7 (a & b) may be pivotally attached on opposing sides of the laryngeal base 2 by snap-fit plastic hinges, longitudinally running hinges, or anything other feature to enable the intended motion. For example, the hinges of FIG. 7 comprise side-by-side cylindrical hinge members 701 separated by a notch 703, with female decent holes 702 entering each end of both hinge members 701 for cooperation with hinge pins on the laryngeal base 2.

In the preferred embodiment, the notch 703 also serves the purpose of allowing installation of a torsion spring 707 about the hinge axis defined by the center of holes 702. The torsion spring 707 allows the lateral stabilizers 7 to automatically deploy from their packaged compact configuration (FIG. 1) to their operationally deployed configuration (FIGS. 2-4). Note that the lateral edges of laryngeal base 2 are fitted with mechanical hard-stops 203 (FIG. 5) to constrain the opening angle of deployment to lit around the patient's neck. The torsion springs also prevent the lateral stabilizers from swinging loosely when deployed, which could complicate use of the device 1.

Lateral stabilizers 7 may also feature an aperture 704 that helps minimize the size of device 1 in its compact configuration. Note that cricoid locator 5 and insertion guide 6 both feature protrusions in the downward direction that may prevent the lateral stabilizers from folding up into the laryngeal base 2 without inclusion of aperture 704. Though it should also be noted that the lateral stabilizers 7 may also be made of a resilient material themselves to improve packaging and conforming to the neck of the patient.

Preferably, the sternal stabilizer 3 (FIG. 6) is configured to be extracted/retracted and automatically locked into place at a desired extension in the illustrated embodiment this is accomplished by forming the sternal stabilizer 3 with two parallel-spaced outwardly-protruding support arms 310 (a & b) each arm being defined by a series of surface features such as ratchet teeth 305 as described above to provide a locking capability through contact with flexible locking detent members 205 of laryngeal base 2. The anus 310 fit slidably into conforming receptacles 210 (a & b) entering distally into the two longitudinal spans 21 of the laryngeal base 2 of FIG. 5. Thus, the arms 310 slide into the receptacles 210 perpendicular to the lateral span 22 which references the patient's jaw with curvature 201 and the patient's neck with curvature 202. The resiliently biased detent members 205 defined by opposing notches 206 in the sidewalk of each receptacle 210 preferably have one or more inwardly protruding teeth or ribs as mentioned above that protrudes into the respective receptacle 210 to engage the ratchet teeth 305 along the corresponding support arm 310 inserted therein. The detent members 205 engage the surface teeth/notches along support arms 310 to resist movement, but the engagement may be overcome by forcible pushing or pulling on arms 310. This allows lengthwise adjustment and provides a tactile indication of the amount adjustment. This configuration makes it easier to position the sternal stabilizer 3 as appropriate against the base of the mandible to accommodate various neck lengths.

Figure 7:
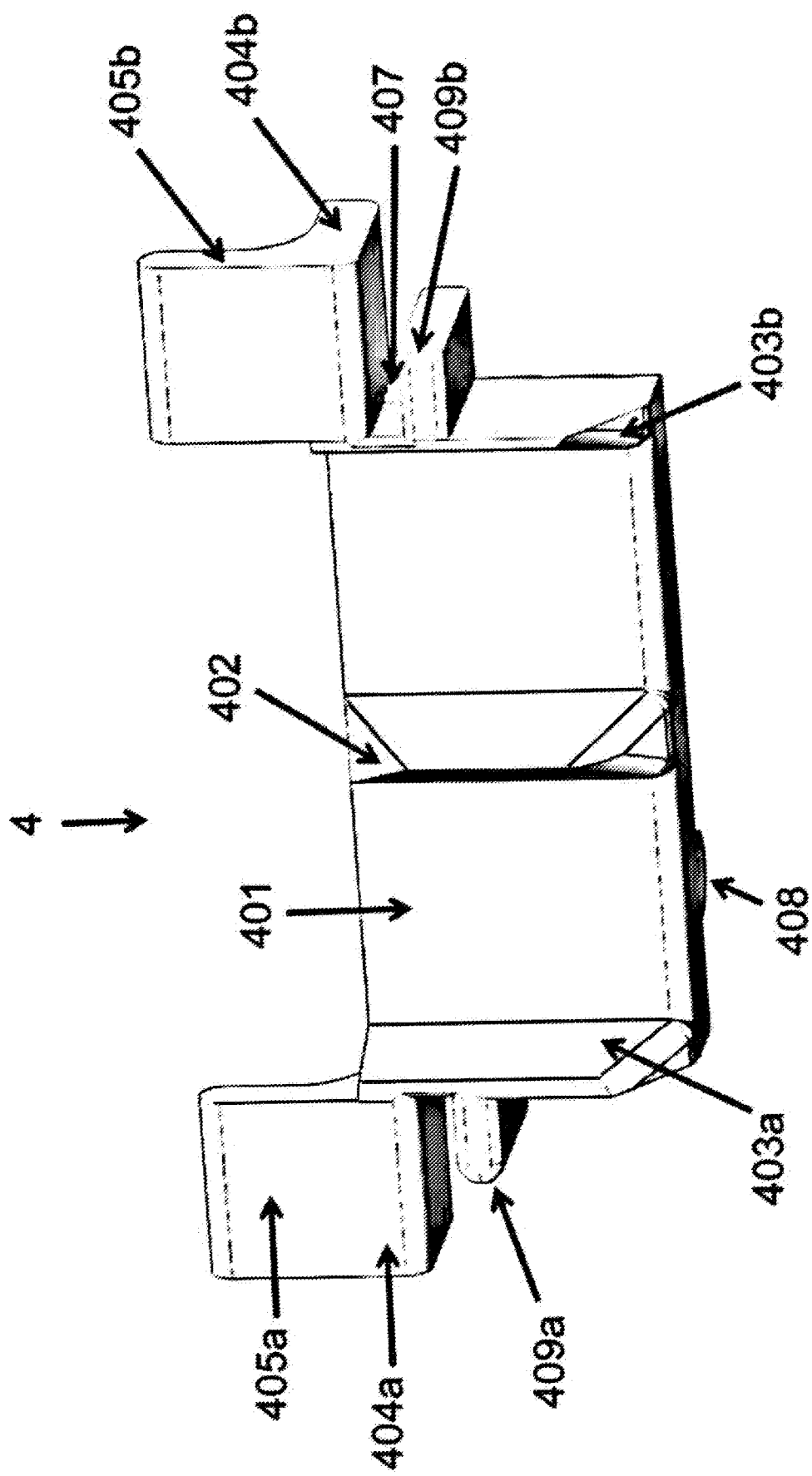
FIG. 7 is a top perspective illustration of the thyroid locator 4 of the airway creation assist device 1 of FIGS. 1-4.
Figure 8:
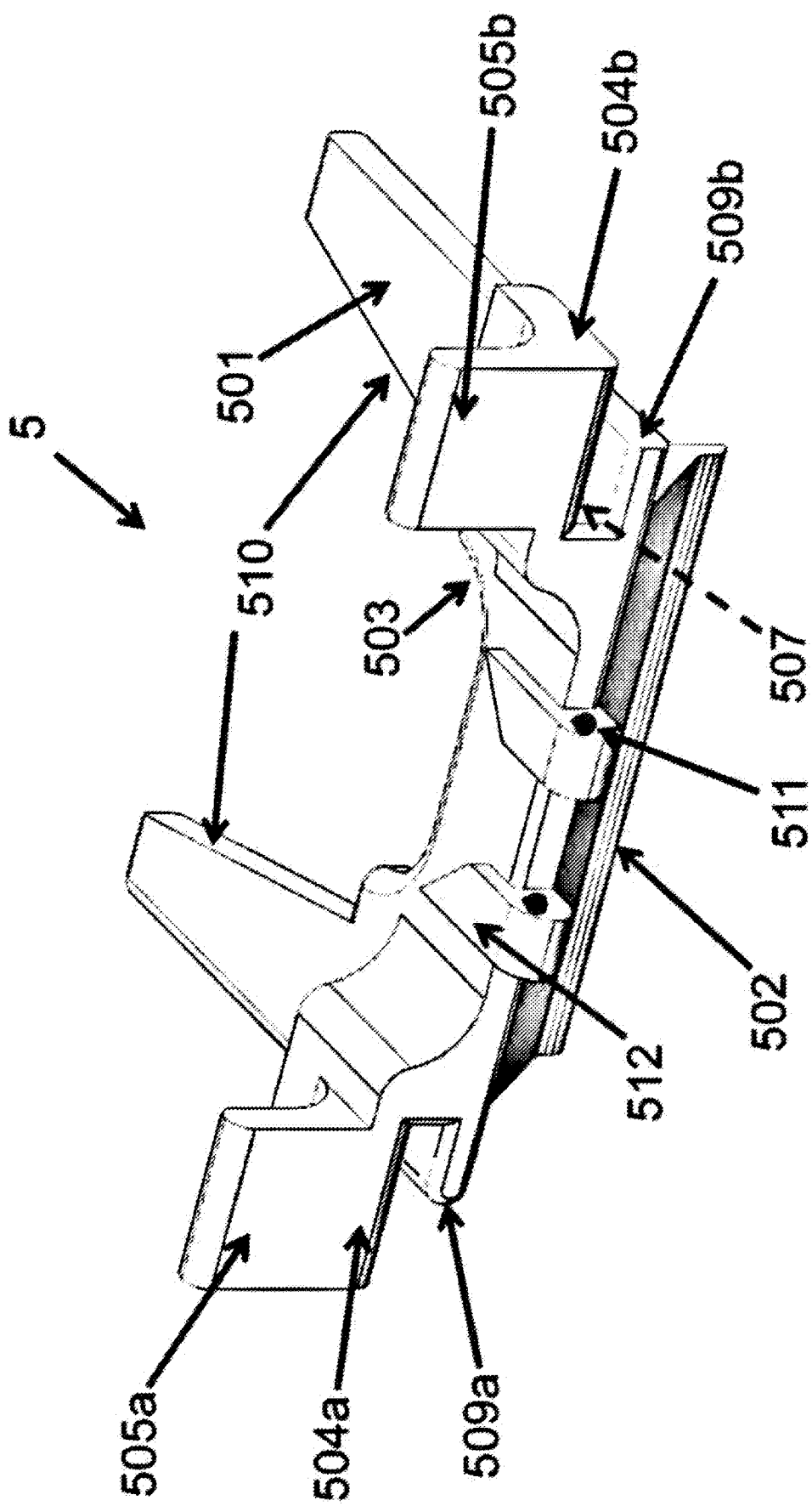
FIG. 8 is a top perspective illustration of the cricoid locator 5 of the airway creation assist device 1 of FIGS. 1-4.

After the laryngeal base 2 has been properly positioned with sternal stabilizer 3 locked in place, both indexed by anatomical features, a thyroid locator 4 as shown in FIG. 7 slidably positioned within the interior of the laryngeal base 2 and is adjusted lengthwise along the neck from the superior-most position in the caudad direction until the lateral span 401 abuts the superior surface of the patient's thyroid cartilage and angled extension 402 engages the thyroid notch. This also provides mid-line alignment of device 1 for performing the procedure. Adjustment of thyroid locator 4 is made through finger tabs 405 (a & b) that extend anteriorly from lateral anterior extensions 404 (a & b). Note that moving thyroid locator 4 in the caudad direction also moves cricoid locator 5 closer to its intended position since the two components are in contact with each other in asymmetrically shaped channels 209 (a & b) of laryngeal base 2 via asymmetrical tabs 409 (a & of thyroid locator 4 and asymmetrical tabs 509 (a & b) of cricoid locator 5.

Once the thyroid locator 4 has stopped against the patient's thyroid cartilage, the cricoid locator 5 of FIG. $ is adjusted lengthwise farther along the patient's neck in the caudad direction (parallel to longitudinal spans 21) and is likewise positioned with reference to anatomical features then locked in position. Cricoid locator 5 comprises a slide platform 501 (shown and described below with regard to FIG. 8) with an insertion guide 6 (FIG. 9) pivotally mounted at one end. The insertion guide 6 is formed as a substantially "U-shaped" collar-receptacle suspended centrally on two opposing hinge-arms 12 extending from the cricoid locator 5.

As seen in FIG. 8, the cricoid locator 5 has two forwardly-protruding asymmetrical runners 509 to slidably fit within tracks 207 of laryngeal base 2. Two upwardly projecting finger tabs 505 (a & b) from lateral extensions 504 (a & b) facilitate this sliding as the component is adjusted by the user. The runners 509 converge on a somewhat semi-circular cutout 503 there between. Opposite cutout 503, the cricoid locator 5 is formed with two protruding hinge-arms 512 that end in as pair of detent hinges 511 for pivotal mounting of insertion guide 6 about its detent hinge 611. As the cricoid locator 5 is adjusted in the caudad direction, downward-protruding tab 502 traverses the skin over the surface of the patient's thyroid cartilage, then the depression over the cricothyroid membrane, and then abuts the superior surface of the cricoid cartilage and stops. At this point, the somewhat semi-circular cutout 503 is directly above, and is effectively "cupping" the cricothyroid membrane, which is the proper procedure site. More medial pressure is applied by the user now to also locking engage the medial teeth 207 of laryngeal base 2 with the corresponding lateral teeth 407 of thyroid locator 4 and 507 of cricoid locator 5. Therefore, the procedure location is identified and the anatomy stabilized.

Figure 9:
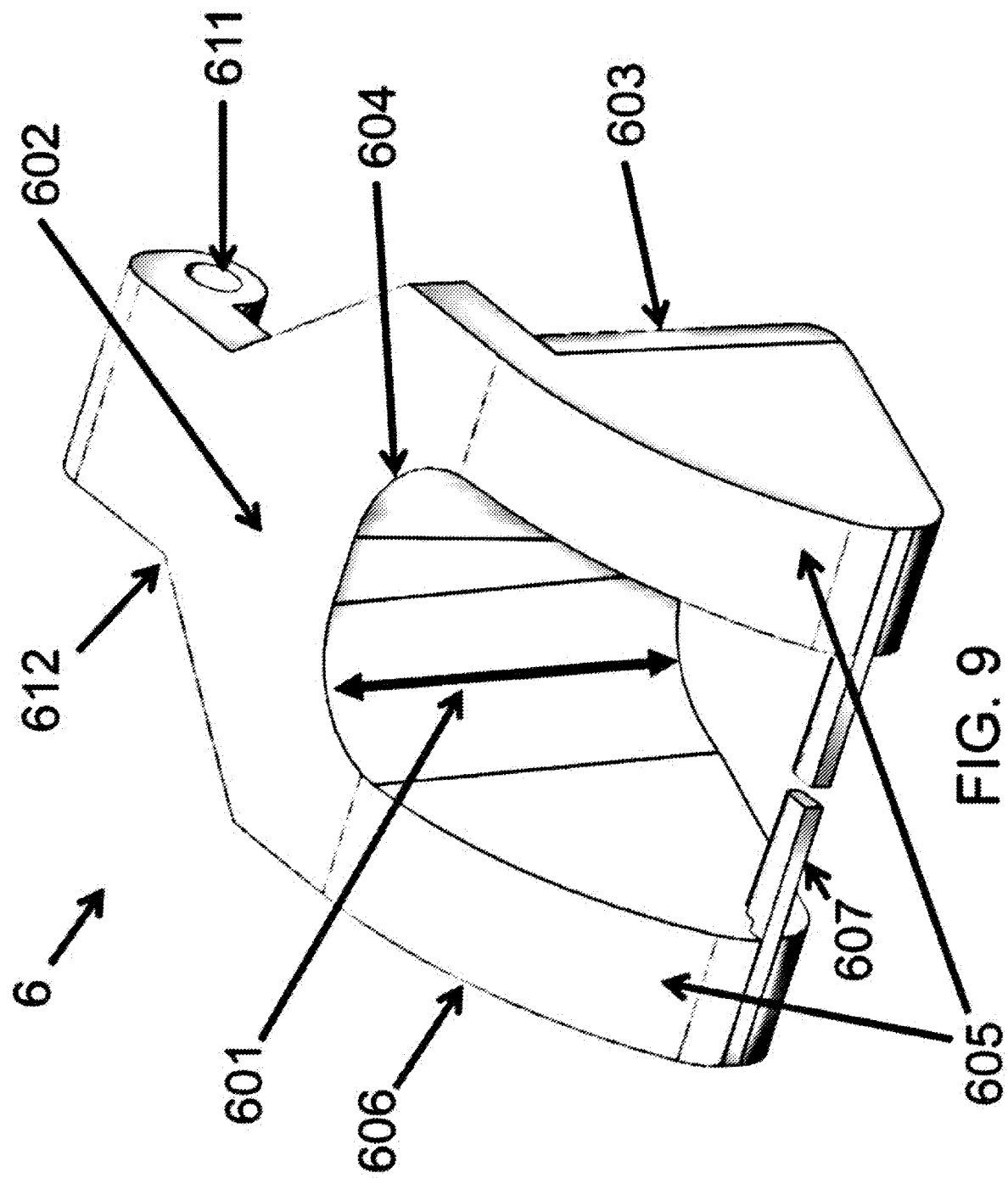
FIG. 9 is a top perspective illustration of the insertion guide 6 of the airway creation assist device 1 of FIGS. 1-4.

As seen in FIG. 9, the insertion guide 6 is configured for pivotable mounting on hinge-antis 512 of cricoid locator 5 within the interior of the laryngeal base 2. The insertion guide 6 is formed as a "U-shaped" collar-receptacle for directing, a cricothyrotomy tube 80 during insertion. With additional reference to FIGS. 1-2, insertion guide 6 is mourned in the hinge-arms 512 extending from the cricoid locator 5 and works as a constraining component to guide obturator 85 and cricothyrotomy tube 80 safely and consistently into the trachea through the cricothyrold membrane. Note that the insertion guide 6 does not physically insert the obturator 85 and cricothyrotomy tube 80. Rather it provides directional guidance to the user, as well as an insertion depth hard-stop. The insertion guide 6 further comprises an arm 602 pivotally mounted on a hinge 611 by, e.g., opposing hinge pins, with an angled feat ire 612 designed to help hold insertion guide 6 in place between hinge-arms 512 once it has been pivoted into the identified position 503. Note that insertion guide 6 has a contour 603 that matches 503 of cricoid locator 5 for added stability between the two components. Insertion guide 6 features a U-shaped collar 605 attached distally at the opposing end of arm 602 to provide directional and angular guidance to insert cricothyrotomy tube 80. While the U-shaped arms 605 provide lateral directional guidance, effectively maintaining mid-line alignment, the base of the "U" 604 provides a caudal constraint.

During insertion, the user is instructed to ensure that the cricothyrotomy tube is pressed against and follows this constraint 604.

The obturator 85 and cricothyrotomy tube 80 are pushed into the patient until the downward-angled tube base 81 abuts the insertion guide arm 602. At this point, the insertion guide 6 provides a mechanical hard-stop 601 for insertion depth to guard against over-insertion and damaging the posterior tracheal wall. After reaching the insertion hard-stop 601, the obturator 85 is removed and the external end of the cricothyrotomy tube 82 is rotated toward the patient's head, while maintaining downward pressure to prevent dislodgement. During this rotation, cricothyrotomy tube 80 will follow the curved contour 606 of U-shaped arms 605 of insertion guide 6. Here, the posterior surface of cricothyrotomy tube base 83 will abut the thyroid locator 4 at the proper angle for advancement farther into the trachea, and ventilation can begin. Note that the insertion guide 6 may also be fitted with break-away safety tabs 607 to prevent cephalad movement of the obturator 85 and cricothyrotomy tube 80 during the procedure, but that will break away during the tube rotation step in the process.

Note that the cricothyrotomy tube 80 may be a commercially-available device with obturator 85.

In an alternative embodiment, the guide arm 602 of insertion guide 6 may be further articulated, in addition to hinge 611, to alter its pivoting motion and/or stage its operation. For example, guide area 602 may be doubly hinged, wherein the first hinge 611 at its base allows successful puncture of the cricothyroid membrane and trachea by the obturator 85 and tube 80, and a second hinge (not shown) above the first hinge 611 allows the tube 80 to be progressed safely into the trachea. In this embodiment, the second hinge may feature a mechanical stop to limit pivoting. Additionally, the doubly hinged arm ma be configured for added safety such that the second hinge is not movable/active until after the first hinge 611 has reached its mechanical stop.

In another alternative embodiment, the guide arm 602, either in the singly or doubly hinged configurations, may also employ a sliding feature such that the obturator 85 and tube 80 can be traversed, into the trachea through a substantially linear type of motion rather than through a pivoting, motion. In this embodiment, the sliding feature may also be restricted from motion until the preceding hinged motion(s) have reached as mechanical stop.

In still another alternate embodiment (described below) insertion guide 6 is replaced with an insertion cartridge that docks with the laryngeal base 2.

All of the foregoing components may be formed of cost-effective bio-compatible materials.

The seven primary components: (1) laryngeal base 2; (2) sternal stabilizer 3; (3) thyroid locator 4; (5) cricoid locator 5; (6) insertion guide 6; and (7) lateral stabilizers 7 (two) essentially combine to form an integrated template that enables rapid and consistent identification of the correct procedure site, that allows the anatomy, site, and device 1 to be stabilized, and that maintains correct alignment about the proper anatomical landmarks to perform the cricothyrotomy procedure using those landmarks, as well as providing a guide for the obturator 85 and cricothyrotomy tube 80, which is easily removable after intubation without dislodging the tube 80 from the patient.

Any suitable airway tube and obturator, (e.g., Quicktrach™ kit, etc., as described above) may be used with an appropriately designed insertion guide 6 to enable safe and consistent intubation. Moreover, when not in use the device 1 folds up into the more compact stowed position shown in FIG. 1. The result is as convenient, easy-to-use handheld device that can perform safe and effective airway creation procedures, such as cricothyrotomies, regardless of the situation or user experience.

Preferably, the device 1 is color-coded, and/or labeled for ease of use.

FIG. 4 illustrates the contour of the downwardly-extending (i.e., posteriorly extending) lateral stabilizer flaps 7 protruding from laryngeal base 2. The lateral stabilizers 7 are designed to provide lateral stability about the patient's neck and to help identify the centerline of the trachea using the trachea itself and the thyroid cartilage as physical references. Clearly visible in the top view of FIG. 4 is the open central region 10, which is configured to replicate/envelope the shape of the relevant anatomy (e.g., thyroid cartilage and cricoid cartilage), which will reside in this region 10 when the device 1 is properly used. Note the flanges 403 of thyroid locator 4 and flanges 510 of cricoid locator 5 partially define this shape, along with cutout 503 and thyroid notch identifier 402.

FIG. 3 details the downward protrusions of: sternal stabilizer 3 which, by virtue of its downward protrusion adds caudal stability and indexes the location of the sternal manubrium; thyroid locator 4 which abuts the superior surface of the thyroid cartilage; and cricoid locator 5 which abuts the superior surface of the cricoid cartilage through its downward extension 502. The sternal stabilizer 3 rests atop the manubrium of the sternum and between the sternocleidomastoid muscles, i.e., fits within the sternal notch, providing the second point of lateral stability in addition to a caudal reference.

Figure 11:
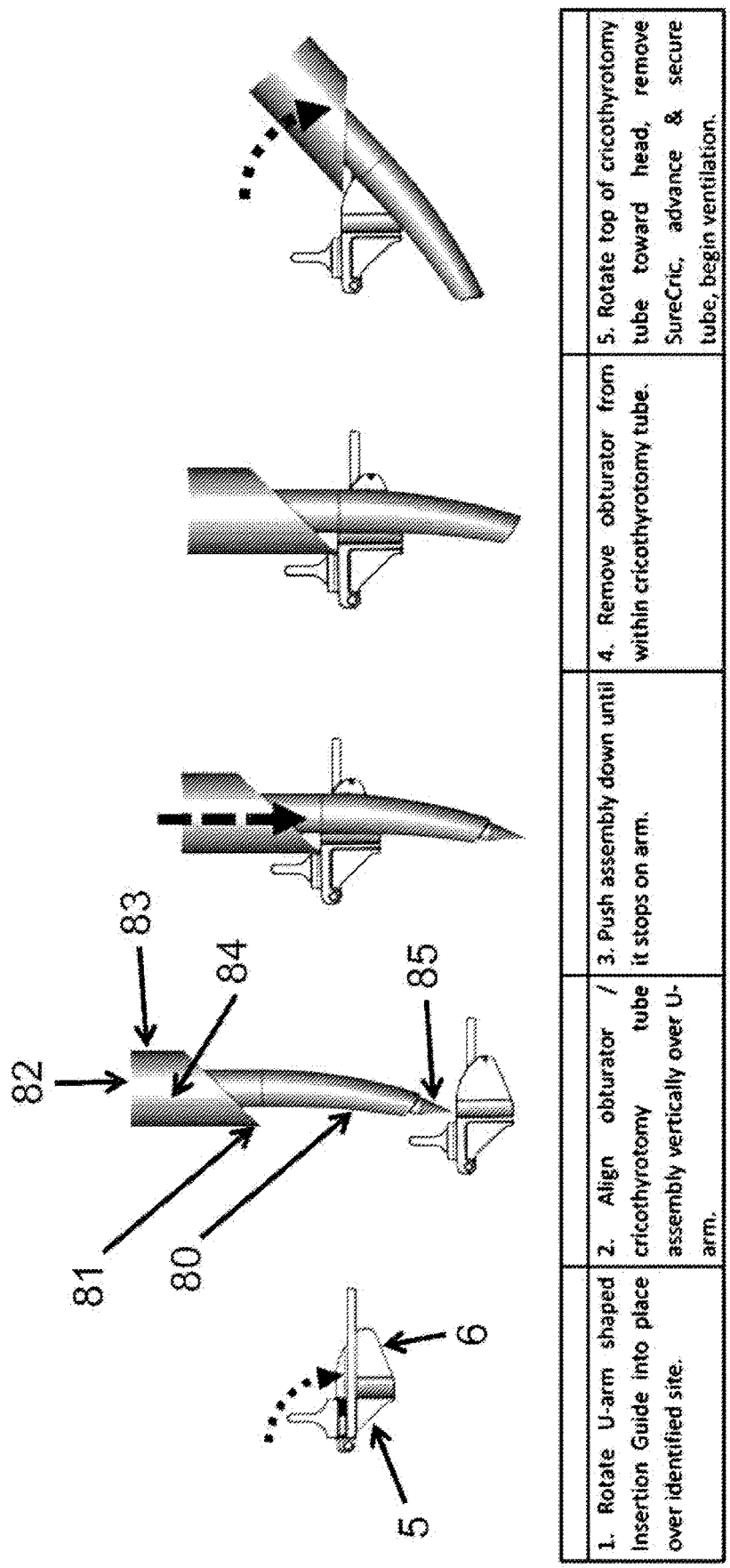
FIG. 11 is a sequential illustration of the airway tube insertion phase of the overall procedure using the preferred embodiment of the device 1 of FIGS. 1-10.

FIG. 11 illustrates the simple 5-step airway tube insertion phase of the overall emergency procedure sequence using the ACAD device 1 described above. One skilled in the art will understand that the tube insertion of FIG. 11 occurs after landmark referencing, site identification, and stabilization.

In an alternative embodiment, rather than using a insertion guide (to guide intubation into the identified insertion site, it may be preferred that once the anatomical landmarks have identified the proper insertion site, a light source (e.g., a laser pointer type device) mourned to the slide platform 503 may mark/illuminate the spot where the procedure is to occur. One skilled in the art will appreciate that this embodiment would require a power source for the illuminated pointer.

The procedure essentially comprises use of the free hand to apply force on the obturator 85 in the airway tube 80 to guide it through the designed insertion path (FIG. 11). The airway tube 80 is a tapered tube in which a sharp, removeable, hollow, conical tip (obturator 85) sits, which functions as its own dilator to puncture and then divide the tissue, while also allowing for aspiration to confirm establishment of the emergency airway.

Figure 12:
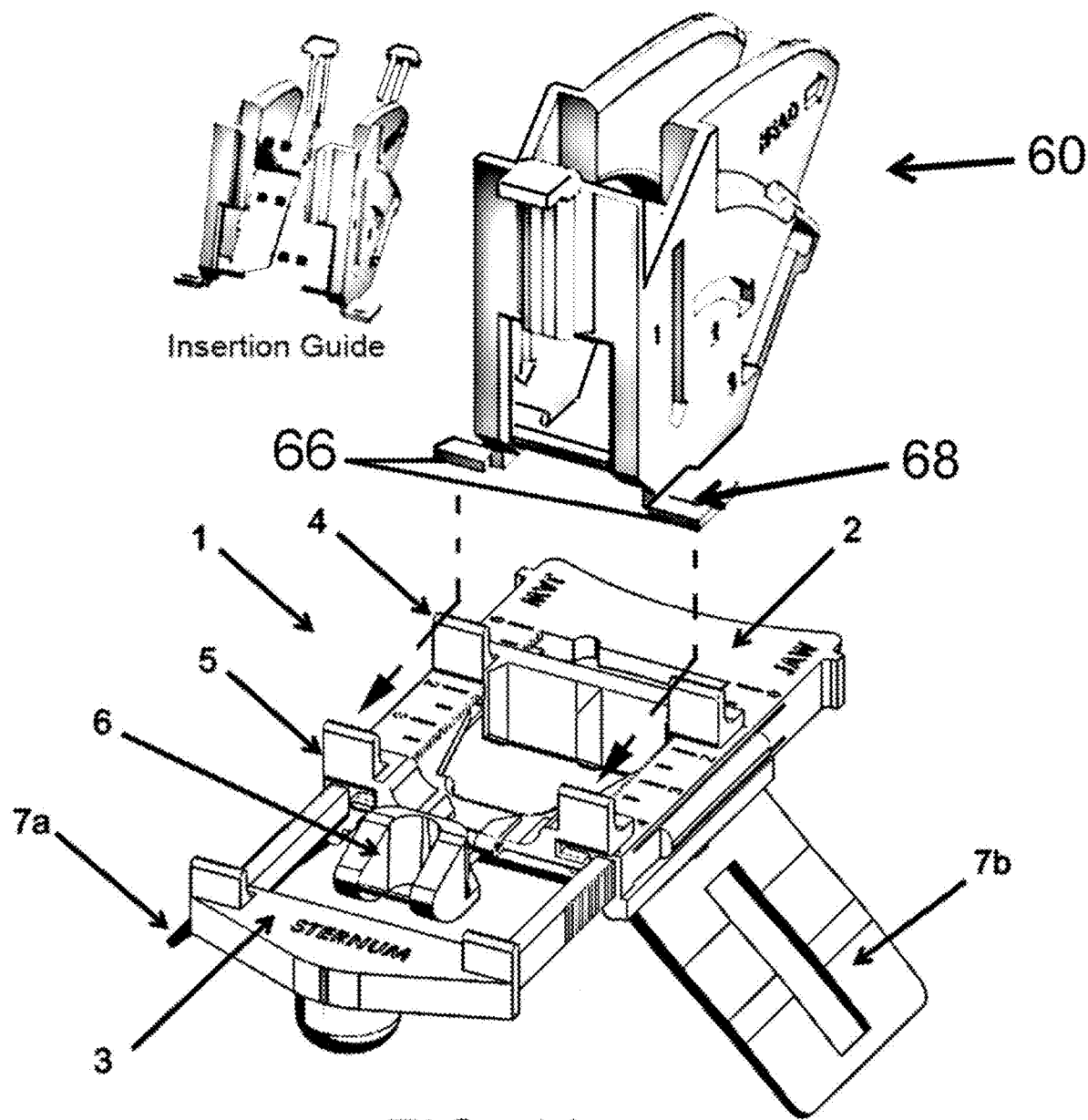
FIG. 12 is a top perspective illustration of an alternate embodiment of the airway creation assist device 1 in a deployed operational configuration.

FIG. 12 shows an alternate embodiment of the device 1, wherein the U-shaped, pivoting, insertion guide 6 has been replaced with a cartridge-like insertion guide 60.

Figure 13:
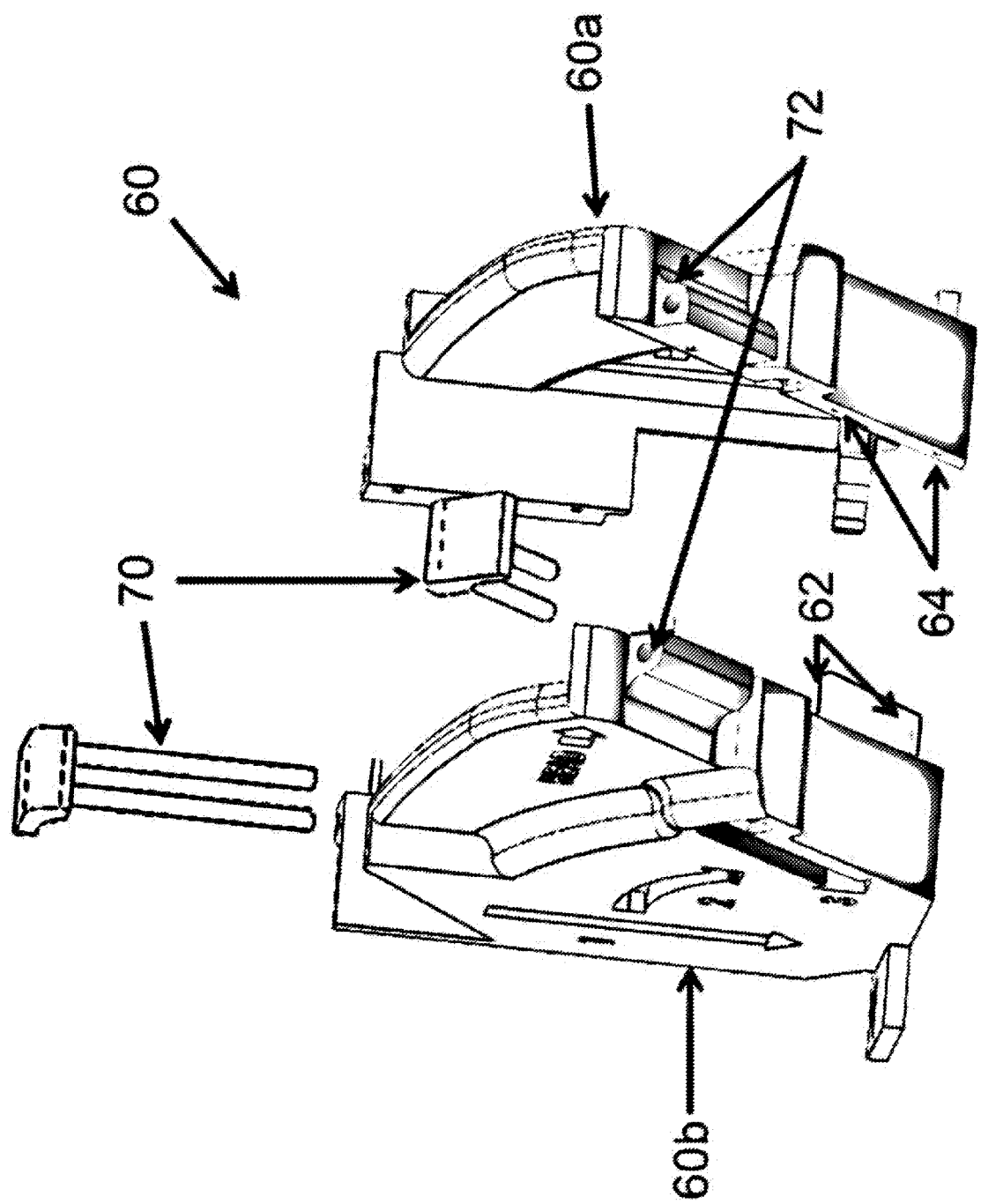
FIG. 13 is a back perspective, exploded illustration of the multiple-piece insertion guide of the alternative embodiment of the device 1 of FIG. 12.

FIG. 13 is a back perspective, exploded illustration of a multiple-piece insertion cartridge 60 designed to dock with laryngeal base 2 according to an alternative embodiment of the invention. Insertion cartridge 60 lends more precision to the ventilation positioning. Insertion cartridge 60 generally comprises two cooperating halves 60a & 60b capable of being fixedly attached together and taken apart at will. For example, the illustrated embodiment does this with male pins 62 on one half 60b and female pins 64 on the other half 60a. To affix halves 60a & 60b together forked coupling pins 70 may be inserted into corresponding receptacles 72 in the opposing halves 60a, 60b.

Figure 14:
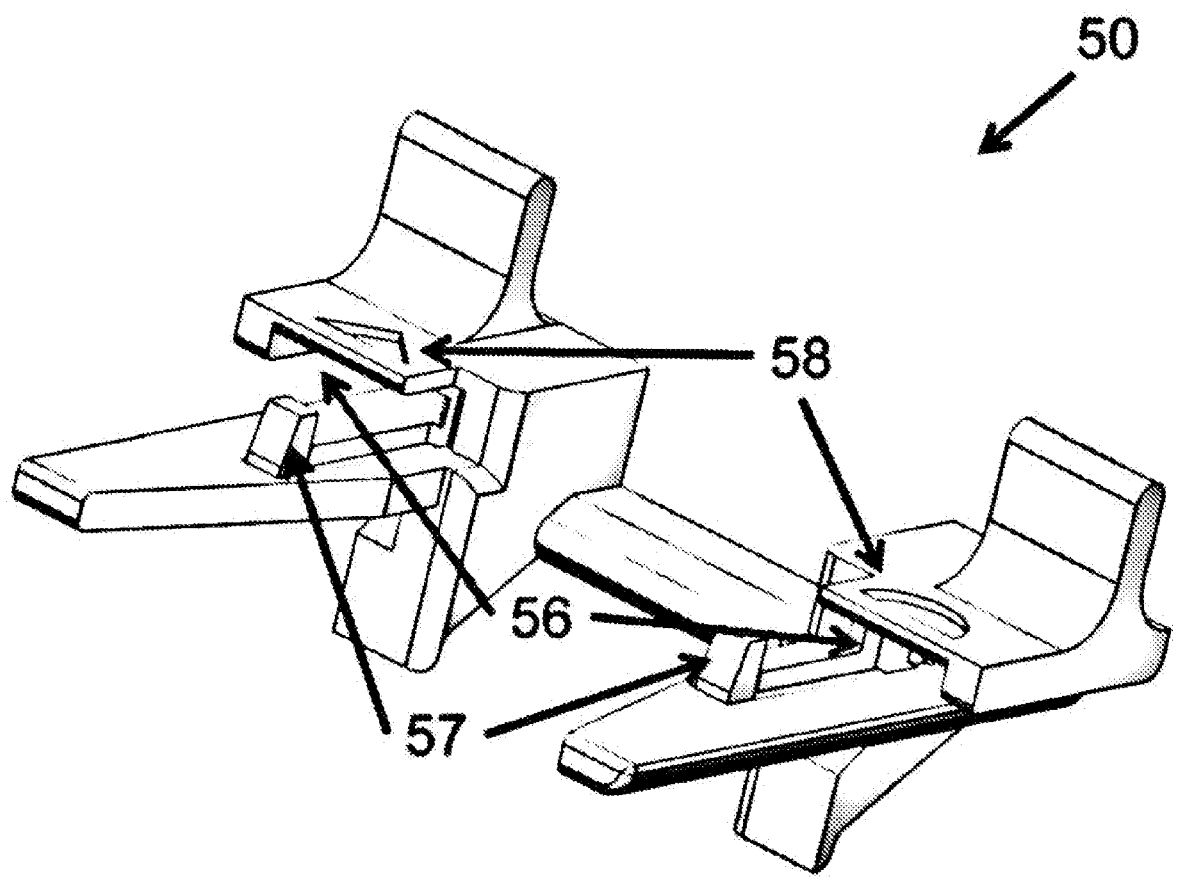
FIG. 14 is a perspective view of alternate embodiment of cricoid locator of the alternate embodiment of the device 1 of FIG. 12.

When joined together, the two halves form a unit that can be docked to the ACAD device 1. Docking may be accomplished with flanges 66 that fit inside the inner tracks 56 of corresponding alternate embodiment of cricoid locator 50 of FIG. 14, while still residing atop laryngeal base 2, likewise slidably seating the insertion cartridge 60 on the mid-line of laryngeal base 2 for cephalo-caudad positioning there along. Annotations 68 of insertion guide 60 may be matched with annotations 58 of cricoid locator 50 to ensure proper orientation of the relative components. Secure seating of insertion guide 60 within cricoid locator 50 is maintained by spring tabs 57, which are pushed down while sliding flanges 66 into tracks 56 and then spring back up to prevent relative motion between insertion guide 60 and cricoid locator 50. The two components can then be slidably positioned as a single unit. When joined together and docked to ACAD device 1 as described above, the two halves 60a, 60b define an interior that effectively forms a template to guide the stepwise placement of a airway tube 80 into the trachea. Once inserted, the two halves 60a, 60b break apart easily and can be removed more easily without accidentally dislodging the inserted tube. Note that insertion guide. 60 has various annotations identifying the correct orientation of the device relative to the patient and the numbered steps of the procedure (1, 2 and 3) using the component. There are also several intuitively (e.g., arrow) shaped windows that accompany these annotations that provide the user with more instructional information on how to perform the procedure as well as allowing the user to see the insertion site and inside the insertion guide 60 during the process.

Figure 15:
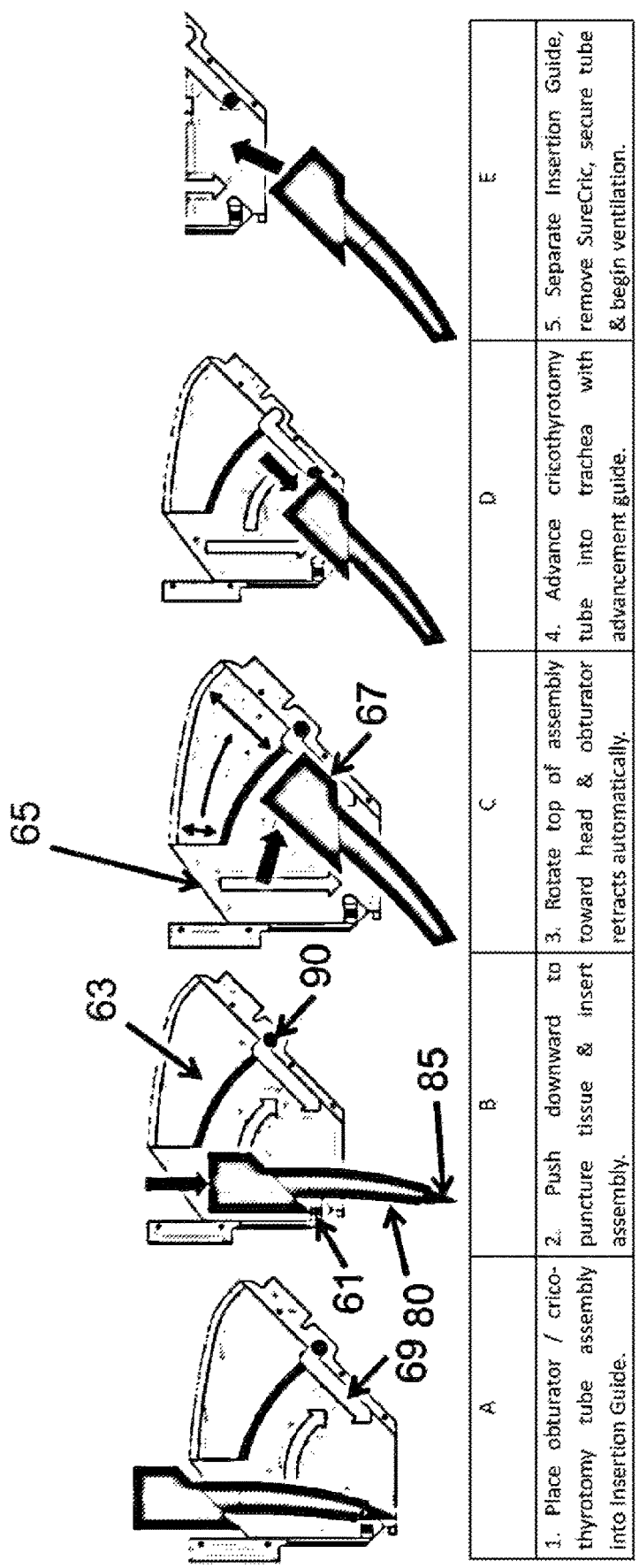
FIG. 15 is a sequential illustration of the airway tube insertion phase of the overall procedure using the alternate embodiment of the device 1 of FIG. 12.

FIG. 15 is a sequential illustration of the airway tube insertion phase of the overall emergency procedure using the insertion cartridge 60, which occurs after landmark referencing, site identification, and stabilization. At FIG. 15(A), the obturator 85/airway tube 80 assembly is inserted endwise down into a vertical channel in the insertion guide 60 and tube base 84 rests on entrance ledge 65 a set distance away from the patient's neck such that the obturator 85 does not yet pierce the skin.

At FIG. 15(B) downward truce is applied to puncture the tissue until the tip of tube base 81 encounters a hard-stop 61 of insertion guide 60 that obstructs further insertion at the proper penetration depth.

At FIG. 15(C) the obturator 85/airway tube 80 assembly is pivoted within the insertion guide 60 until it encounters a sidewall 67 which serves as a second hard-stop indicating the correct angle for which the airway tube 80 can be farther advanced down the trachea. During this pivoting action obturator removal feature 63 automatically retracts the obturator tip to prevent posterior tracheal all injury. It does so by creating a track (between the two halves 60a & 60b) with two arcs whose relative spacing increases in the cephalad direction. In this way, the proximal end of the obturator 85 is pulled upward and the tip is retracted to within the airway tube 80. Once the second hard-stop 67 is reached, the entire obturator is then easily removed.

At FIG. 15(D) the user advances the airway tube 80 downward within the insertion guide 60 by sliding transverse pin 90 along its angled track in insertion guide 60. This implants the tube 80 at exactly the correct depth.

At FIG. 15(E) the user separates the halves of the insertion cartridge 60a, 60b removes the cartridge 60 and device 1, secures the ventilation tube 80 to the skin and begins ventilation.

Figure 16:
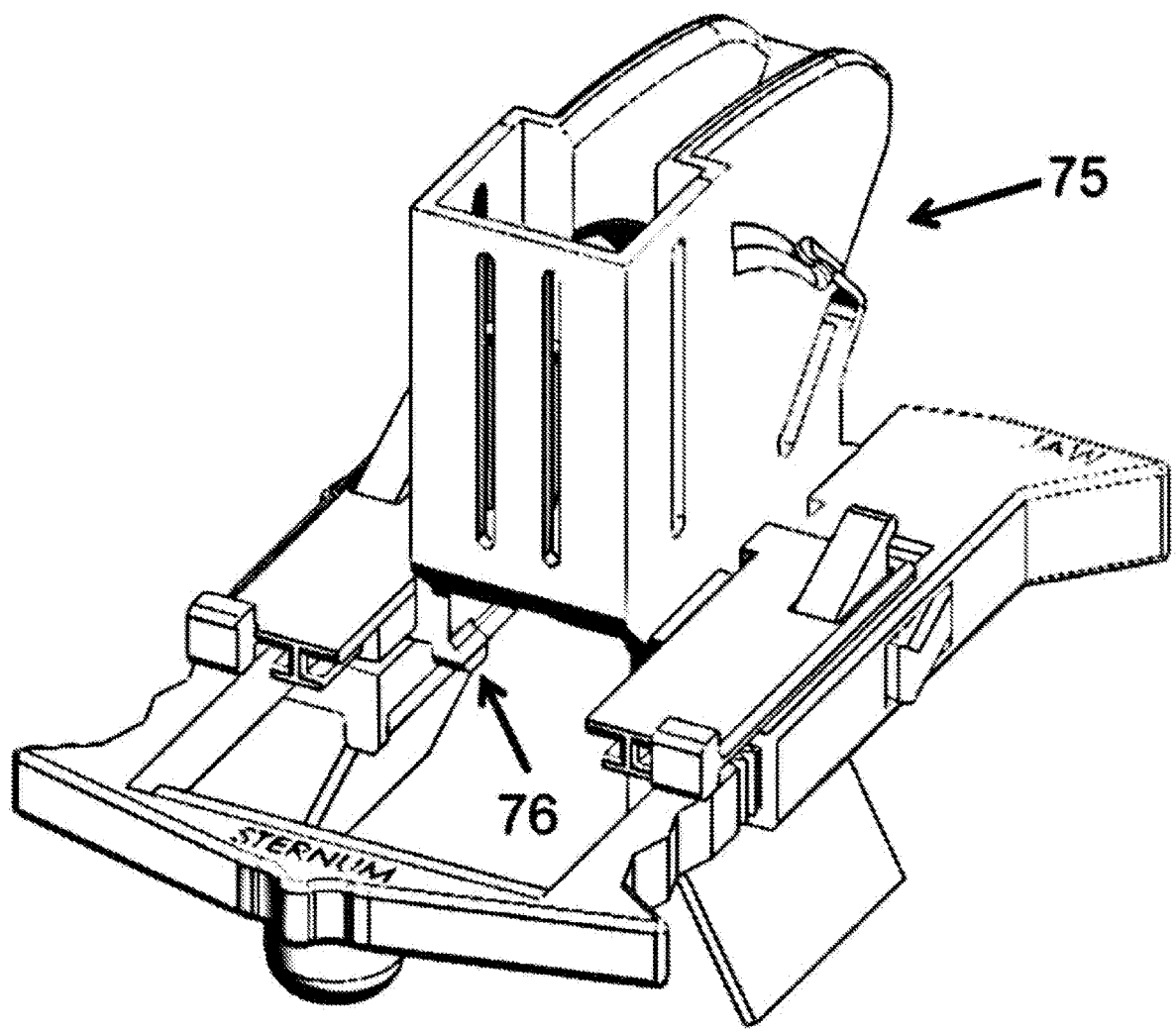
FIG. 16 is a top perspective illustration of yet another alternate embodiment of the airway creation assist device 1 in a deployed operational configuration.

FIG. 16 presents yet another alternative embodiment of device 1, wherein the cartridge-like insertion guide 75 is a single piece that slidably engages with laryngeal base 2 through the inner tracks 209. In this embodiment the cricoid locator 5 is not present because insertion guide 75 has features 76 on each side intended to properly identify the depression of the cricothyroid membrane. The internal features of insertion guide 75 are the same as was described for insertion guide 60, and the intubation procedure is the same as in FIG. 15, except for FIG. 15(E). In this embodiment, insertion guide 75 does not split into two halves, so the entire device 1 is simply lifted off of the patient's neck at the same time as a single unit, leaving the airway tube 80 properly inserted.

Figure 17:
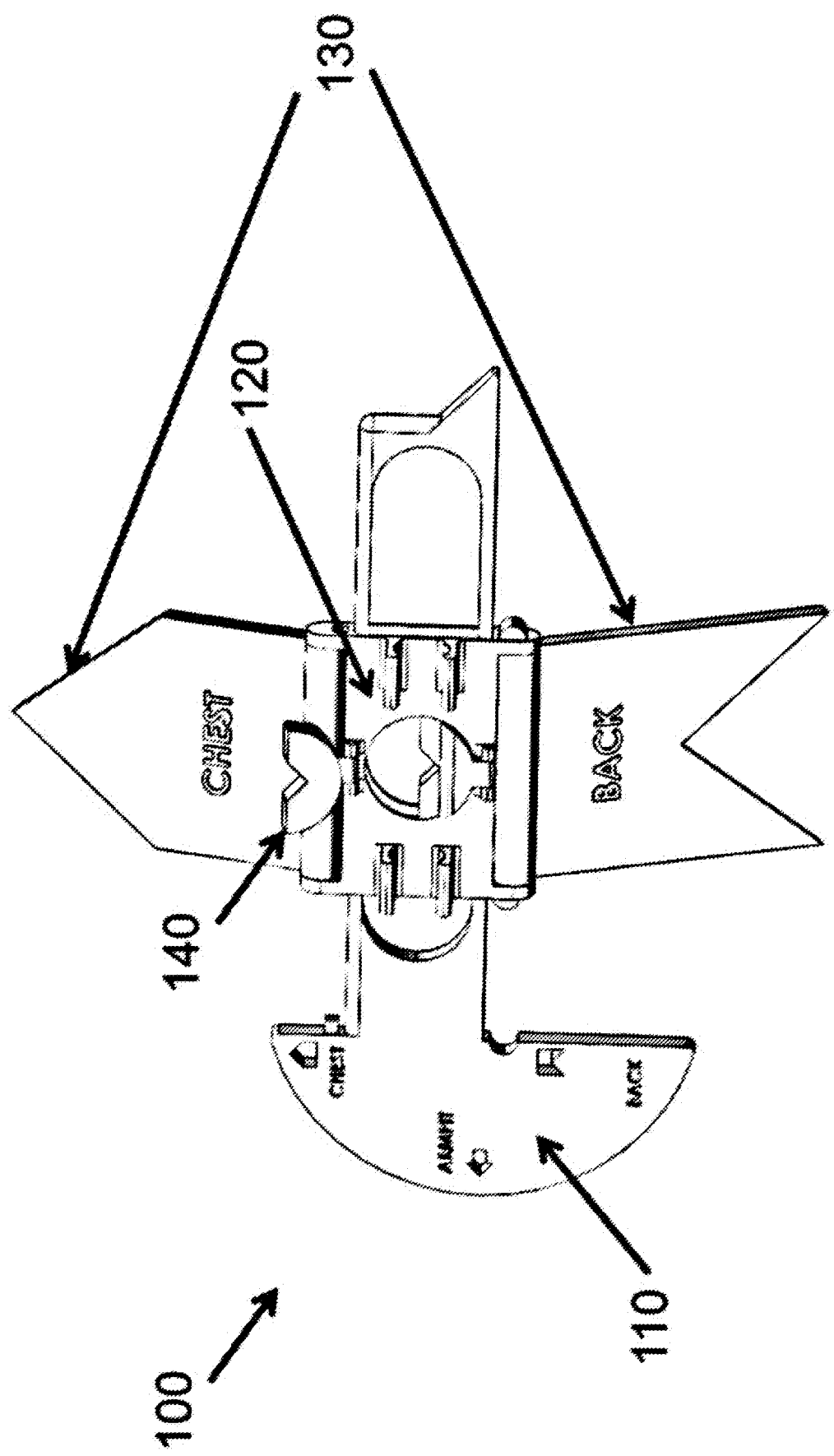
FIG. 17 is a side view of an alternate embodiment of the medical assist device, shown for a needle and chest tube decompression procedure on the patient's right side.

Yet another alternate embodiment of a medical assist device 100 is shown in FIG. 17. In this embodiment the device 100 is configured to provide assistance in performing chest decompression. The device 100 comprises a base component 110, a length adjustment component 120, flanges 130, and pivoting guides 140.

Figure 18:
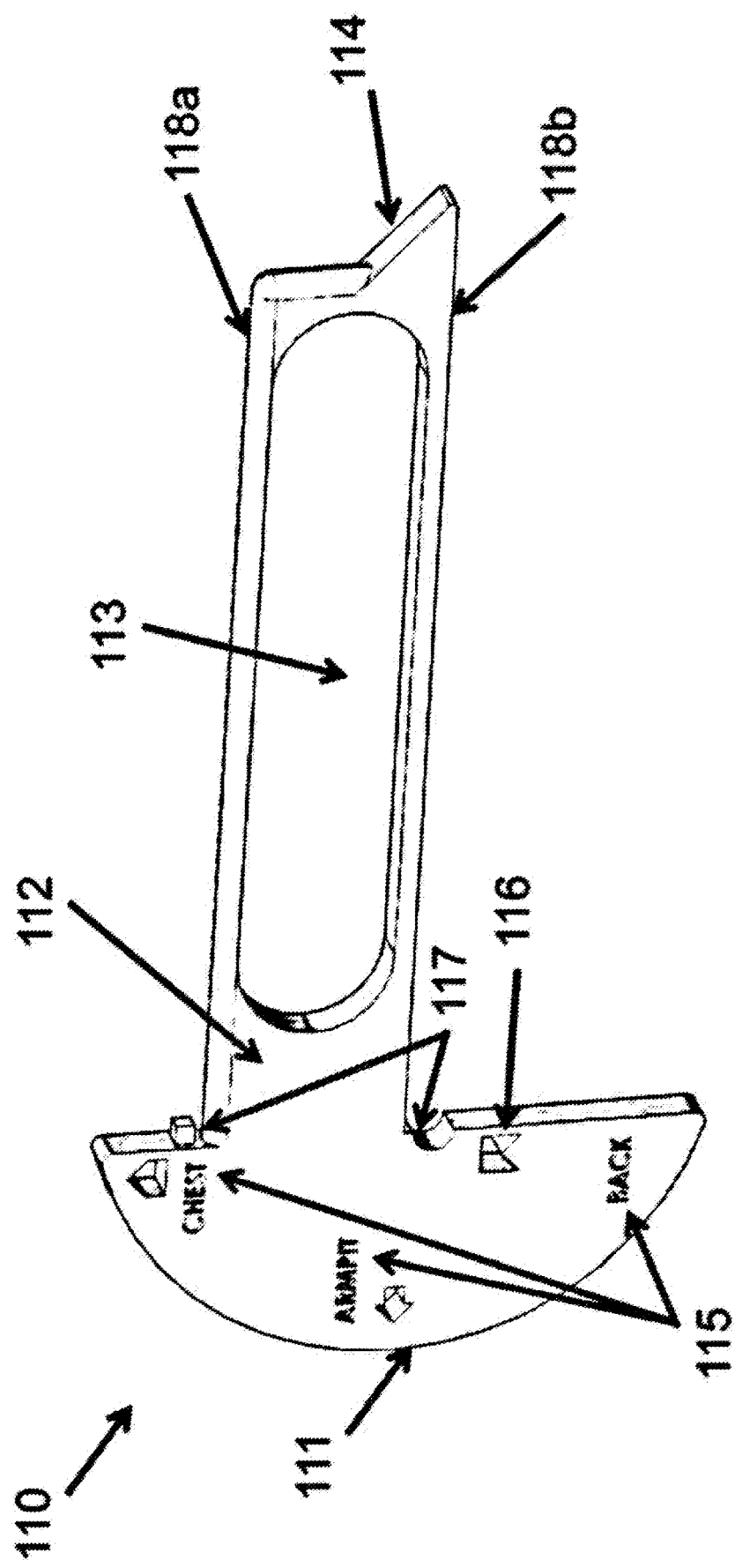
FIG. 18 is a side view of the base template component of the alternate embodiment of FIG. 17.

As seen in FIG. 18, the base 110 or this alternate embodiment is defined by a superior arch segment 111 configured to reference and identify the anatomical shape of the axilla of a patient and an inferiorly extending segment 112. The inferiorly extending segment 112 contains an internal slot 113 to accommodate different patient sizes, and terminates at the inferior end with a pointer 114, which during operation is pointed toward the patient's iliac crest (i.e. pelvis), serving as a second anatomical reference point to ensure proper alignment of the device 100.

To provide the user with information on correct orientation of the device 100 relative to the patient, the base component 110 may additionally feature descriptive annotations 115 including "chest", "armpit" and "back". Further, the base 110 may feature geometrical shapes 116 that provide guidance to the user on correct device orientation, which may also align with other device components, such as the flanges 130, when assembled correctly. Safeguards to prevent incorrect assembly may also be included, such as asymmetrical shapes 118 on the edges of the inferiorly extension segment 112 that will only fit with the length adjustment component 120 in the correct orientation. Alternate geometric shapes and male-female mating characteristics 117 may be employed for the purposes of correct assembly and component orientation as well.

Note that the annotations 115 of the base component preferably appear on both lateral faces of the base 110 because it must be applicable (annotations visible to user) to both the left and right side of the patient. The geometric shapes 116 preferably extend through the thickness of the base 110 for the same purpose, though this is not necessary as long as they are visible to the user on both sides of the base 110.

For the anatomical referencing of the base component 110 shown in FIG. 18, the inferiorly extending segment 112 is biased anteriorly (i.e., toward the chest) since this alternate embodiment 100 is intended for chest/needle decompression through the $4^{th}$ or $5^{th}$ intercostal space along the anterior axillary line. For other such medical procedures, however, this bias may not be necessary and different anatomical landmarks may be referenced, within the same type of device.

With the base component 110 providing anatomical references for the axillary line through the patient's axilla and iliac crest, and being anterior to that line, movement of the length adjustment component 120 provides the next anatomical reference with assistance from the flanges 130. The flanges 130 are preferably shaped to resemble a pointer, such as an arrow, wherein the anterior flange ends in a point and the posterior flange does not. Recall that the base component 110 may contain geometric annotations 116 that coincide with the shapes of the flanges 130 when properly oriented. The pointer defined by the flanges 130 moves via the length adjustment component 120 until the pointer is aligned with the patient's nipple line, as this defines the $4^{th}$ or $5^{th}$ intercostal space, into which the needle is to be placed to accomplish decompression.

Figure 19:
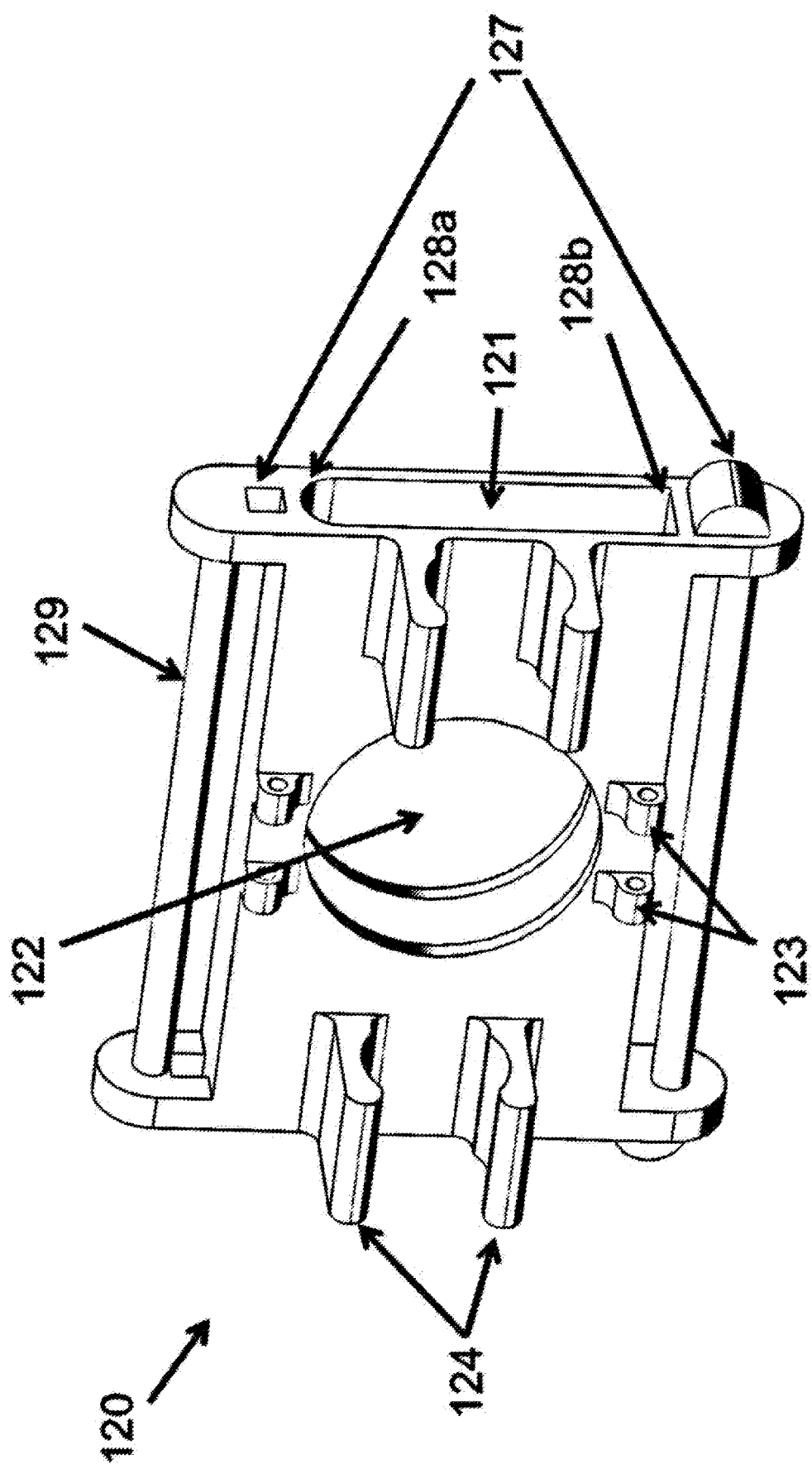
FIG. 19 is a side view of the adjustment component of the alternate embodiment of FIG. 17.

The length adjustment component 120 is pictured alone in FIG. 19. This component is defined by an internal channel 121 that fits, preferably slidably, over the interiorly extending segment 112 of base component 110. As such, the anterior and posterior edges of this channel feature geometric asymmetry, shown here as a rounded face 128a and a flat face 128b to prevent incorrect assembly over the correspondingly asymmetric laces 118a and 118b of extension 112. Offering more, and redundant, information to the user, this component also has different geometrically shaped features and male-female characteristics 127 to further distinguish the anterior thin) posterior, which mate with related base components 117. These features give the adjustment component 120 asymmetry about the component's coronal plane.

Contrary to the base component having the same global orientation relative to the patient (e.g., arch 111 being superior), the adjustment component 120 has a relatively flat side that is placed against the patient's body, regardless of the device 100 being on the left or right side, and a non-flat side (pictured) that contains other design features and is not intended to contact the patient. Hence, the inclusion of and utility of the noted asymmetric design features which ensure this component orientation. This gives the adjustment component 120 asymmetry about the component's sagittal plane.

The adjustment component 120 does have symmetry about its transverse plane, however, because it must be able to point out the correct insertion site on both sides of the patient.

The adjustment component 120 is further defined by a center opening 122, preferably large enough to fit a human finger to allow for palpation to confirm that the proper site has been identified prior to inserting the needle. This opening 122 slides along the slot 113 of base component 110 when being adjusted for the patient size.

The outer surface of the adjustment component 120 is fitted with hinge arms 123 which allow a pivoting connection to insertion guides 140. The pivoting guides 140 can be folded into the opening 122 in a compact stowed state of the device 100 and folded out to expose the opening when aliening the device for the procedure. Once the device is properly positioned, the guides 140 can be folded back into the opening 122, where they can provide guidance on proper needle insertion depth, as well as holding the proximal end of the needle in a secure position once the distal end has been fully inserted. While the figure shows the insertion guides as two substantially semi-circular shaped pieces the device could use a single piece that folds into and out from the opening as required for the procedure without changing the invention.

The outer surface of the adjustment component 120 may also be fitted with laterally extending tabs 124. These tabs may be configured to hold the needle in its case securely with the device 100 until the user needs to perform the procedure on a patient. As shown these tabs 124 are flexible tabs that allow the needle case to snap into and out of place easily.

The anterior and posterior sides of the adjustment component 120 also have hinges 129 that allow pivoting connection of the flanges 130. The flanges 130 pivot about these hinges 129 to adjust for the size of the patient's torso. Preferably, the flanges 130 are a resilient material that allows for a more compact stowed configuration of the device 100, as well as allowing them to conform to the shape of the patient's body. Further, the body-side of the flanges 130 preferably has adhesive backing with easy peel-off coverings, such that the flanges 130 can secure the device 100 to the patient after needle insertion, thereby providing more stability to the inserted needle.

As pictured in FIG. 17, the outer surface of the flanges 130 may also contain annotations, redundant or otherwise, that provide useful information to the user. The figure shows body labels, but instructions for use or images could also be used instead without changing the invention.

It should now be apparent that the devices for assisting, medical procedures in the Various embodiments described above will significantly improve the success rate and effectiveness of performing the relevant procedure.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

INDUSTRIAL APPLICABILITY

Studies suggest that many casualties could be avoided if interim tools and procedures could be implemented to allow non-experts to perform certain procedures before the injured patient can be transported to higher level of care facility/provider. What is needed is an assist device for guiding performance of certain medical procedures, including cricothyrothmies, tracheostomies, tracheotomies, chest decompression, thoracostomies, thoracotomies, and other percutaneous procedures. The present invention is an innovative device for performing such procedures with universal applicability that significantly improves the success rate and avoids complications when performing the procedures.

What is claimed is:

1. A device for assisting with a medical procedure on a human patient, comprising:
   a base extending from a first end to a second end and having at the first end a first reference configured to index a referenced position relative to an anatomical landmark of said human patient by alignment with said anatomical landmark; and
   an adjustable component integrated with said base and translatable thereon along a translation path extending between said first end and said second end of said base to identify a procedure site on said human patient, said adjustable component including a lateral span across said translation path, a second reference on said lateral span configured for indexing a human cricoid cartilage over said translation path, and a third reference configured to index said procedure site when said second reference indexes said human cricoid cartilage.

2. The device of claim 1, wherein said medical procedure is one of a cricothyrotomy, tracheostomy or tracheotomy.

3. The device of claim 1, wherein said anatomical landmark for said referenced position of said base is a human thyroid cartilage.

4. The device of claim 1, wherein said anatomical landmark for said referenced position of said base is the region inferior to a human mandible.

5. The device of claim 1, wherein said adjustable component is integrated slidably with said base, and said base includes measuring indicia indexing sliding displacement of the adjustable component along said translation path.

6. The device of claim 1, wherein said procedure site is a human cricothyroid membrane.

7. The device of claim 1, wherein said procedure site is an interspace of human tracheal rings.

8. The device of claim 1, further comprising at least one flange attached to said device for stabilizing said device in said referenced position with respect to said procedure site.

9. The device of claim 8, wherein said at least one flange is movable with respect to said base.

10. The device of claim 1, wherein said lateral span bridges two longitudinal spans.

11. The device of claim 1, wherein said referenced position is about a human larynx.

12. The device of claim 1, wherein said second reference is configured to index the cricoid cartilage through physical abutment therewith.

13. The device of claim 1, wherein said adjustable component and said base in combination surround a constrained area which identifies said procedure site.

14. The device of claim 1, wherein said adjustable component is removable from said base.

* * * * *